United States Patent
Miao et al.

(10) Patent No.: US 11,679,162 B2
(45) Date of Patent: Jun. 20, 2023

(54) ANTI-5T4 ANTIBODY-DRUG CONJUGATE AND USE THEREOF

(71) Applicant: HANGZHOU ADCORIS BIOPHARMA CO., LTD., Hangzhou (CN)

(72) Inventors: Zhenwei Miao, Zhejiang (CN); Tong Zhu, Zhejiang (CN); Alisher B. Khasanov, Zhejiang (CN); Sheldon Cao, Zhejiang (CN); Zhaohui Li, Zhejiang (CN); Min Wu, Zhejiang (CN)

(73) Assignee: HANGZHOU ADCORIS BIOPHARMA CO., LTD., Hangzhou (CN)

( * ) Notice: Subject to any disclaimer, the term of this patent is extended or adjusted under 35 U.S.C. 154(b) by 810 days.

(21) Appl. No.: 16/476,487

(22) PCT Filed: Jan. 8, 2018

(86) PCT No.: PCT/CN2018/071774
§ 371 (c)(1),
(2) Date: Jul. 8, 2019

(87) PCT Pub. No.: WO2018/127175
PCT Pub. Date: Jul. 12, 2018

(65) Prior Publication Data
US 2019/0374651 A1 Dec. 12, 2019

(30) Foreign Application Priority Data
Jan. 8, 2017 (CN) .......................... 201710011890.X

(51) Int. Cl.
| | | |
|---|---|---|
| *A61K 47/68* | (2017.01) | |
| *A61P 35/00* | (2006.01) | |
| *A61K 31/7034* | (2006.01) | |
| *A61K 38/08* | (2019.01) | |
| *C07K 16/30* | (2006.01) | |
| *A61K 39/00* | (2006.01) | |

(52) U.S. Cl.
CPC ...... *A61K 47/6853* (2017.08); *A61K 31/7034* (2013.01); *A61K 38/08* (2013.01); *A61K 47/6803* (2017.08); *A61P 35/00* (2018.01); *C07K 16/3007* (2013.01); *A61K 2039/505* (2013.01)

(58) Field of Classification Search
CPC ............ A61K 47/6803; A61K 47/6853; A61K 31/7034; A61K 38/08; A61K 2039/505; A61P 35/00; C07K 16/3007
See application file for complete search history.

(56) References Cited

U.S. PATENT DOCUMENTS

2012/0251558 A1   10/2012   Gerber et al.

FOREIGN PATENT DOCUMENTS

| CN | 105288644 A | 2/2016 | | |
|---|---|---|---|---|
| EP | 2 694 111 B1 | 8/2016 | | |
| EP | 3 130 356 A1 | 2/2017 | | |
| WO | WO-2016022939 A1 | * 2/2016 | ............. | C07K 16/30 |
| WO | WO-2016123412 A1 | * 8/2016 | ......... | A61K 47/6811 |

OTHER PUBLICATIONS

Beck A, Haeuw JF, Wurch T, Goetsch L, Bailly C, Corvaia N. The next generation of antibody-drug conjugates comes of age. Discov Med. Oct. 2010;10(53):329-39. PMID: 21034674. (Year: 2010).*
Lichtman MA. A Bacterial Cause of Cancer: An Historical Essay. Oncologist. May 2017;22(5):542-548. doi: 10.1634/theoncologist. 2017-0007. Epub Apr. 21, 2017. PMID: 28432224; PMCID: PMC5423514. (Year: 2017).*
Wan Y, Li Y, Yan C, Yan M, Tang Z. Indole: A privileged scaffold for the design of anti-cancer agents. Eur J Med Chem. Dec. 1, 2019;183:111691. doi: 10.1016/j.ejmech.2019.111691. Epub Sep. 11, 2019. PMID: 31536895. (Year: 2019).*
Rashid HU, Xu Y, Muhammad Y, Wang L, Jiang J. Research advances on anticancer activities of matrine and its derivatives: An updated overview. Eur J Med Chem. Jan. 1, 2019;161:205-238. doi: 10.1016/j.ejmech.2018.10.037. Epub Oct. 19, 2018. PMID: 30359819. (Year: 2018).*
Garewal HS, Ramsey L, Kaugars G, Boyle J. Clinical experience with the micronucleus assay. J Cell Biochem Suppl. 1993;17F:206-12. doi: 10.1002/jcb.240531031. PMID: 8412196. (Year: 1993).*
Sapra et al., "Long-term Tumor Regression Induced by an Antibody-Drug Conjugate That Targets 5T4, an Oncofetal Antigen Expressed on Tumor-Initiating Cells," Mol. Cancer Ther., 12(1), pp. 38-47 (2013).
International Search Report mailed in International Patent Application No. PCT/CN2018/071774 (dated Apr. 10, 2018).
Munson et al., "Ligand: a versatile computerized approach for characterization of ligand-binding systems," Anal. Biochem., 1980, 107:220-39.

* cited by examiner

*Primary Examiner* — Adam Weidner
*Assistant Examiner* — Laura Ann Essex
(74) *Attorney, Agent, or Firm* — Michael Best & Friedrich LLP

(57) ABSTRACT

Provided in the present invention is an anti-5T4 antibody-drug conjugate and the use thereof. In particular, provided in the present invention is an anti-5T4 antibody-drug conjugate. Also provided in the present invention are the pharmaceutical use of the anti-5T4 antibody-drug conjugate and the effect thereof in inhibiting or preventing tumors.

20 Claims, 3 Drawing Sheets
Specification includes a Sequence Listing.

ANTI-5T4 ANTIBODY-DRUG CONJUGATE AND USE THEREOF

CROSS-REFERENCE TO RELATED APPLICATION(S)

This application is a U.S. national stage filing under 35 U.S.C. § 371 of International Patent Application No. PCT/CN2018/071774, filed on Jan. 8, 2018, which claims the benefit of Chinese Patent Application No. 201710011890.X, filed on Jan. 8, 2017, the entire contents of each of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 15,929 bytes ASCII (Text) file named "P2019-0985-1PCUS-208330-9009-US01-SEQ-LIST-07-08-19.txt," created on Jul. 8, 2019.

FIELD OF INVENTION

The present invention relates to the field of bio-medicine and, in particular, to an anti-5T4 antibody-drug conjugate.

BACKGROUND OF INVENTION

The human 5T4 carcinoembryonic antigen is a highly glycosylated transmembrane glycoprotein having a molecular weight of approximately 72 kDa and encoded by TPBG gene (trophoblast glycoprotein gene). 5T4 was first discovered in embryonic development and is highly expressed in placental trophoblast cells. Generally absent in normal tissues, 5T4 exists only in certain special epithelia, such as basal lamellar squamous epithelium, glandular and ductal epithelium, secondary retinal neurons and olfactory bulbs. Later, 5T4 was found to be expressed in many cancer types, including ovarian cancer, colorectal cancer, gastric cancer, kidney cancer, prostate cancer, etc., and overexpression of 5T4 in tumors has been associated with disease progression, which may play a role in affecting the connection between tumor cells, cell morphology, movement and adhesion, which in turn promotes distant metastasis, but the specific regulatory mechanisms are not fully understood. But it is obvious that 5T4 is a very attractive target for cancer targeted therapy. Several anti-5T4 antibodies have been reported, including murine or humanized monoclonal antibodies.

5T4 has been proposed as a design target of therapeutic drugs, such as fusion of a Fab fragment of an anti-5T4 antibody with a superantigen, and activating T cells with a superantigen to generate an immune response. For example, a single-chain anti-5T4 antibody scFv-Fc is fused with human pancreas Ribonuclease to form a fusion protein which uses human pancreatic ribonuclease to degrade RNA, thereby causing tumor cells to preferentially die due to disruption of the translation process.

For example, in CAR-T therapy, a vector encoding a chimeric antigen receptor targeting 5T4 is transduced into T cells of parent. The modified T cells can recognize and bind to the 5T4 antigen on tumor cells, thereby killing tumor cells, and the extracellular ligand binding region of the chimeric antigen receptor can be a scFV of an anti-5T4 monoclonal antibody. Additionally, the recombinant 5T4 vaccine is also tried for cancer treatment.

Another successful strategy in the development of cancer-targeted therapies is the use of antibody as a carrier to carry small, toxic molecules into cancer cells and then the dissociated small molecules are used to kill cancer cells. There are currently two antibody-drug conjugates (ADC) used for cancer targeted therapies-Adcetris and Kadcyla. Antibody drug conjugates targeting 5T4 have been described, for example huA 1-mcMMAF (US2012251558), an antibody drug conjugate which is formed by linking the tubulin inhibitor MMAF to the humanized anti-5T4 monoclonal antibody A1 by conventional antibody disulfide bond reduction and in which an antibody molecule is linked to different number (such as 2-8) of MMAFs with an average DAR of 4., clinically showed relatively good safety in phase I (2015 ASCO). Antibody drug conjugates have been showing a significant therapeutic effect on the tumor, and therefore, those skilled in the art are committed to developing new, more effective antibody drug conjugates.

SUMMARY OF INVENTION

The purpose of the invention is to provide an anti-5T4 antibody-drug conjugate and therapeutic application thereof.

In the first aspect of the invention, it provides an antibody-drug conjugate or a pharmaceutically acceptable salt thereof, wherein the antibody-drug conjugate comprises an antibody and a drug coupled with the antibody, and the antibody comprises a heavy chain variable region and a light chain variable region, wherein, the heavy chain variable region comprises three complementary determining regions:

```
CDR1:
GFTFSSYE

CDR2:
ISSSGSTI
and

CDR3:
AREMQFGWELLGAFDI;
``` wherein, the light chain variable region comprises three complementary determining regions:

```
CDR1':
QSVSSSY

CDR2':
GAS
and

CDR3':
QQYGSS.
```

In another preferred embodiment, the sequence of the heavy chain variable region of the antibody is shown in SEQ ID NO. 7.

In another preferred embodiment, the sequence of the light chain variable region of the antibody is shown in SEQ ID NO. 8.

In another preferred embodiment, the antibody comprises the heavy chain as shown in SEQ ID NO. 9.

In another preferred embodiment, the antibody comprises the light chain as shown in SEQ ID NO. 10.

In another preferred embodiment, the drug is a small molecule drug selected from the group consisting of:

Duostatin 5, MMAF, Duostatin 14, Duomycin 2, Duomycin 4, Calicheamicin, and Amanitine.

In another preferred embodiment, the structure of the antibody-drug conjugate is as shown in Formula I:

Ab-(L-D)n    I wherein:
Ab is an antibody;
L is absent or a linker connecting the antibody and the drug;
D is a small molecule drug that inhibits tumor cells;
n is the number of drug coupled to the antibody;
"-" is a bond or a linker.

In another preferred embodiment, the light chain constant region of the antibody-drug conjugate is coupled with at least one drug molecule (preferably one drug molecule per light chain constant region), and the drug molecule is linked to a lysine site in the light chain constant region.

In another preferred embodiment, the light chain constant region of the antibody comprises EKH motif and the drug molecule is linked to a lysine (K) site in the motif.

In another preferred embodiment, the light chain constant region of the antibody comprises YEKHK motif and the drug molecule is linked to the first lysine (K) site in the motif.

In another preferred embodiment, the light chain constant region of the antibody comprises ADYEKHK motif and the drug molecule is linked to the first lysine (K) site in the motif.

In another preferred embodiment, the drug molecule is a small molecule drug that inhibits tumor cells.

In another preferred embodiment, n is the average number of coupled drugs in the antibody-drug conjugate, preferably n is from 1 to 4, preferably from 1.5 to 3.5, and more preferably from 1.8 to 2.

In another preferred embodiment, D is selected from the group consisting of: Duostatin 5, MMAF, Duostatin 14, Duomycin 2, Duomycin 4, Calicheamicin, and Amanitine.

In another preferred embodiment, the structure of the antibody-drug conjugate is as shown in Formula III:

Ab-(-L$^1$—L$^2$—D)$_n$    III wherein, the structure of L$^1$—L$^2$ is selected from L-1, L-2 or L-3:

(L-1)

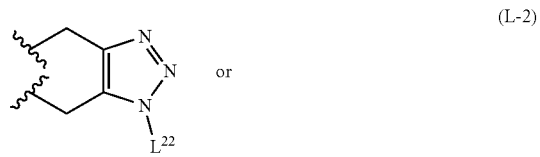
(L-2)

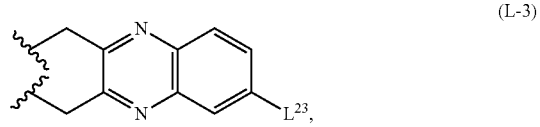
(L-3)

wherein each of L$^{21}$, L$^{22}$, of L$^{23}$ is independently a linker selected from the group consisting of: —(CH2)n-, —(CH2CH2O)n-, Val-Cit, Ala-Ala-Asn, and a combination thereof;

Ab, D, and n are defined as above;

the wavy line indicates the connection position with antibody.

In another preferred embodiment, the antibody-drug conjugate is selected from the group consisting of: ZV0508, ZV0512, ZV0513, ZV0501, ZV0503, ZV0504, ZV0517, ZV0518, ZV0505, ZV0516, ZV0515, and ZV0519;

wherein the structure of conjugate ZV0508 is shown as follows:

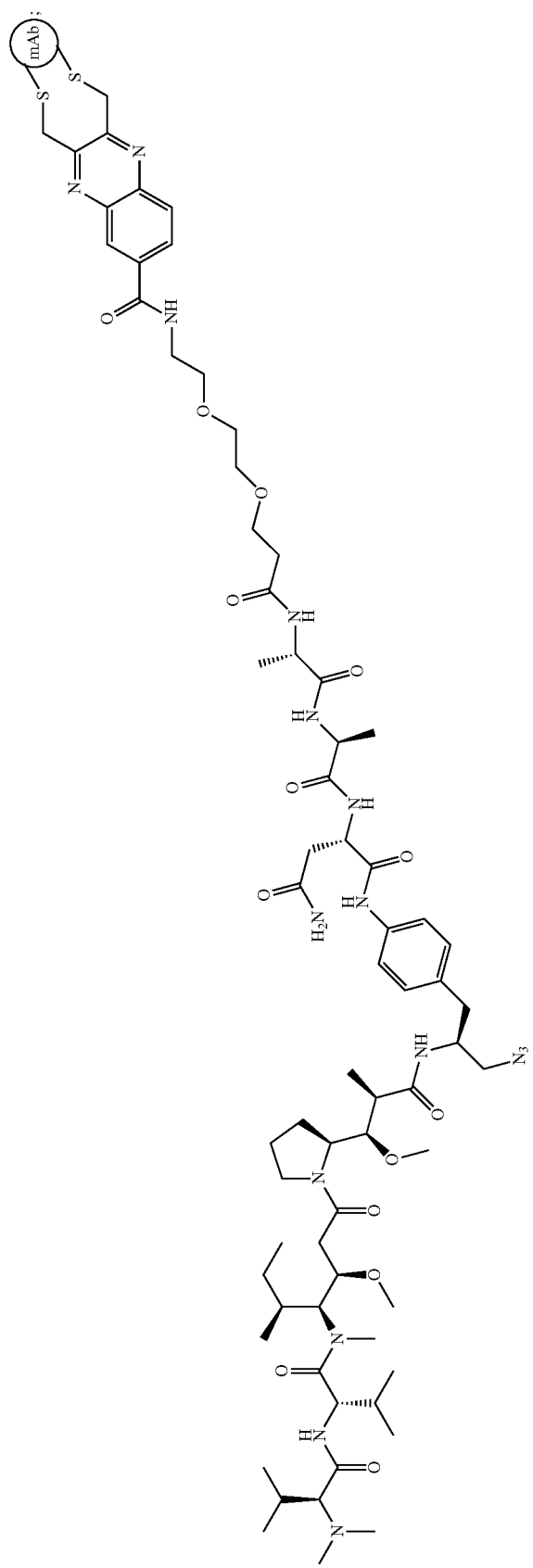

the structure of conjugate ZV0512 is shown as follows:
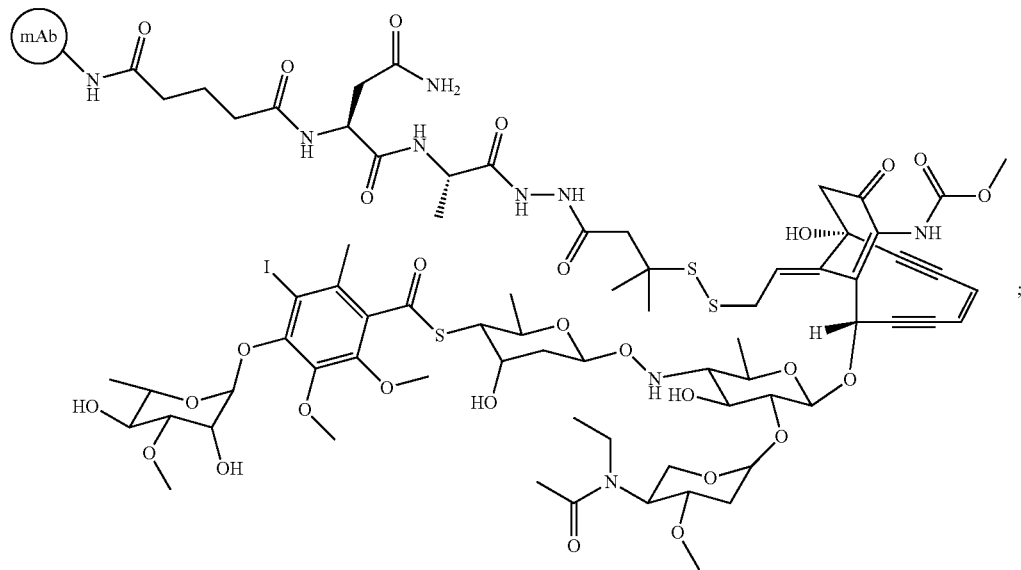
the structure of conjugate ZV0513 is shown as follows:
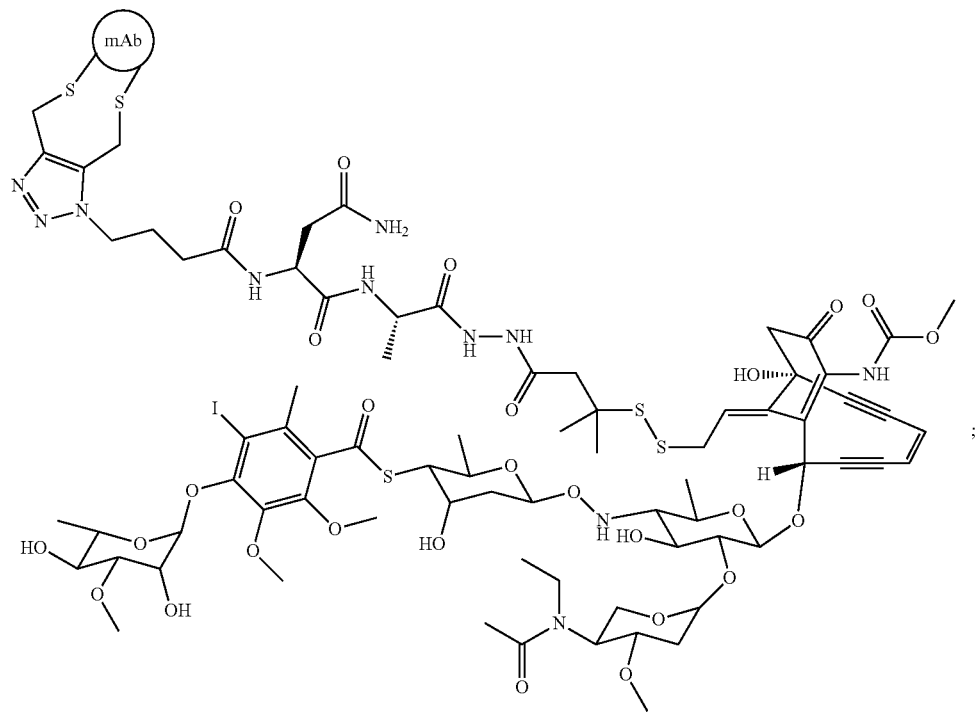

the structure of conjugate ZV0501 is shown as follows:
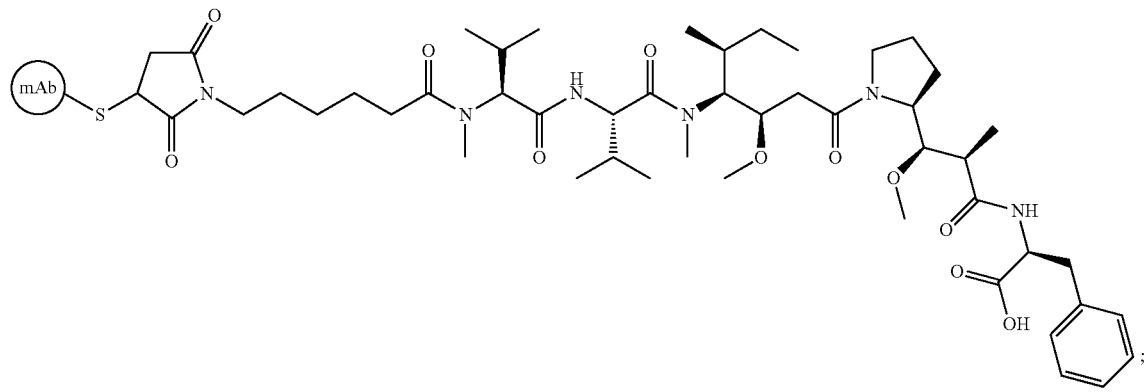 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)CC(SC)C1=O)C(C)C]
the structure of conjugate ZV0503 is shown as follows:
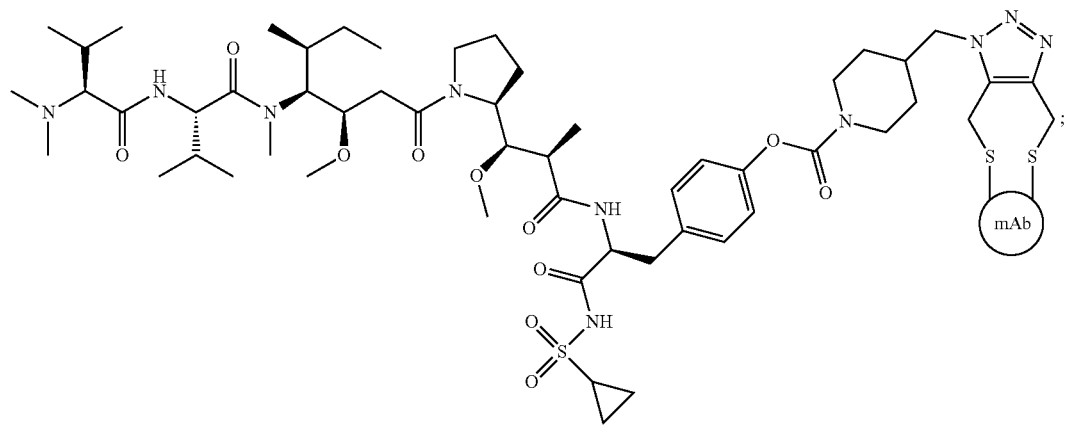 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(Cn3nnc(CSC)c3CSC)CC2)cc1)C(=O)NS(=O)(=O)C1CC1)OC)N(C)C(=O)[C@@H](NC(=O)[C@H](C(C)C)N(C)C)C(C)C]
the structure of conjugate ZV0504 is shown as follows:
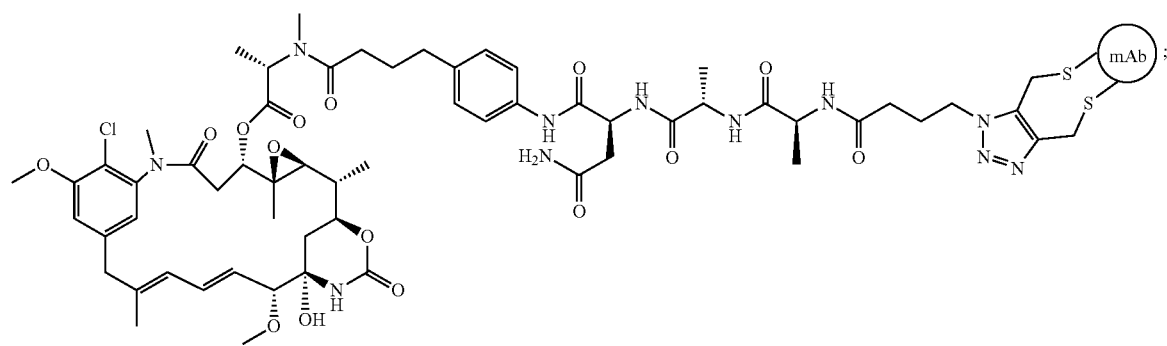

the structure of conjugate ZV0517 is shown as follows:
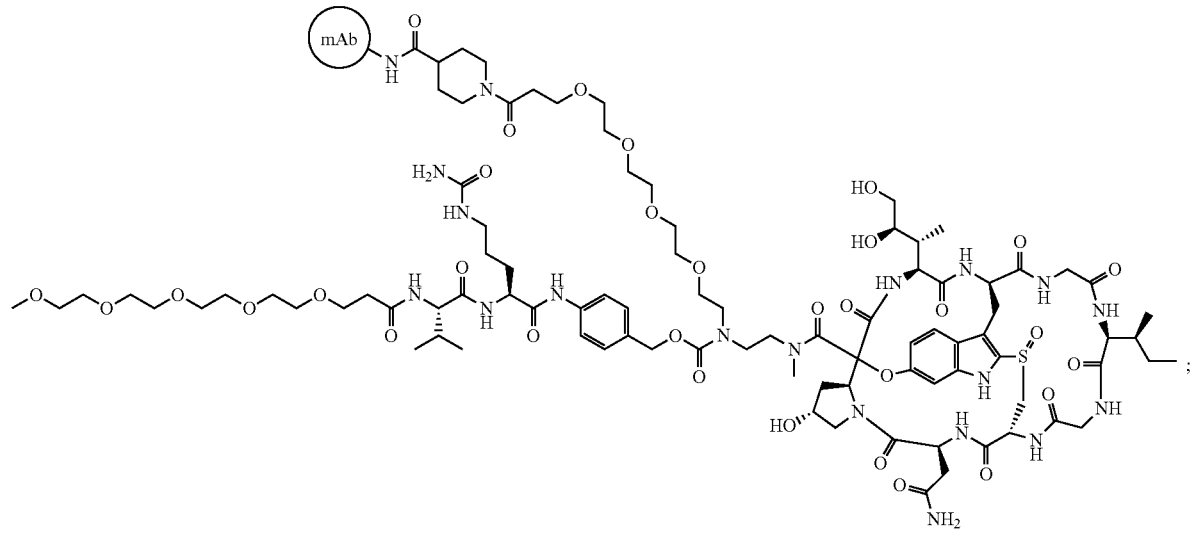 [SMILES: CC[C@H](C)[C@@H]1NC(=O)CNC(=O)[C@H]2Cc3c4[nH]c5cc(ccc35)OC(C(=O)N(C)CCN(CCOCCOCCOCCOCCC(=O)N3CCC(C(=O)NC)CC3)C(=O)OCc3ccc(NC(=O)[C@H](CCCNC(N)=O)NC(=O)[C@@H](NC(=O)CCOCCOCCOCCOCCOC)C(C)C)cc3)(C(=O)N[C@@H]([C@@H](C)[C@@H](O)CO)C(=O)N2)[C@@H]2C[C@@H](O)CN2C(=O)[C@H](CC(N)=O)NC(=O)[C@H](CS4=O)NC(=O)CNC1=O]
the structure of conjugate ZV0518 is shown as follows:
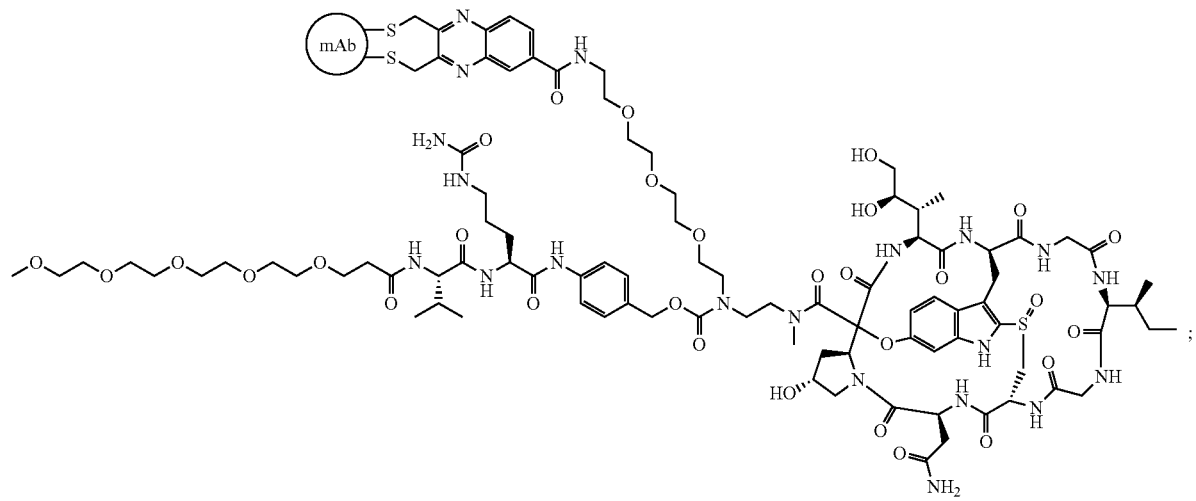 [SMILES: CC[C@H](C)[C@@H]1NC(=O)CNC(=O)[C@H]2Cc3c4[nH]c5cc(ccc35)OC(C(=O)N(C)CCN(CCOCCOCCOCCNC(=O)c3ccc5nc(CSC)c(CSC)nc5c3)C(=O)OCc3ccc(NC(=O)[C@H](CCCNC(N)=O)NC(=O)[C@@H](NC(=O)CCOCCOCCOCCOCCOC)C(C)C)cc3)(C(=O)N[C@@H]([C@@H](C)[C@@H](O)CO)C(=O)N2)[C@@H]2C[C@@H](O)CN2C(=O)[C@H](CC(N)=O)NC(=O)[C@H](CS4=O)NC(=O)CNC1=O]
the structure of conjugate ZV0505 is shown as follows:
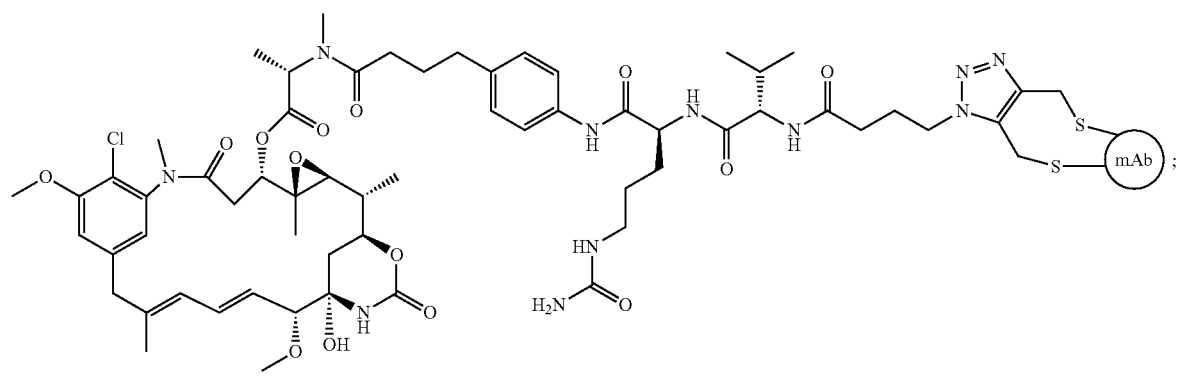

the structure of conjugate ZV0516 is shown as follows:
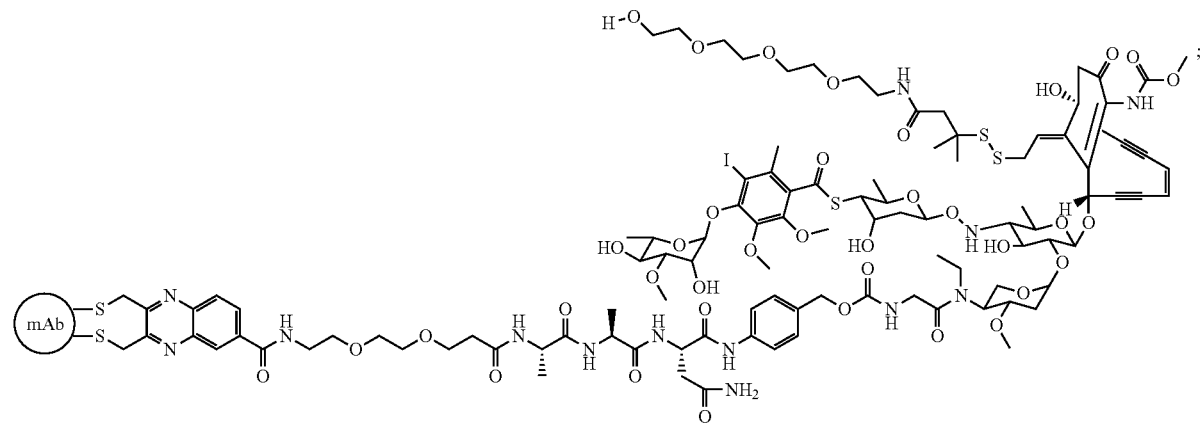
the structure of conjugate ZV0515 is shown as follows:
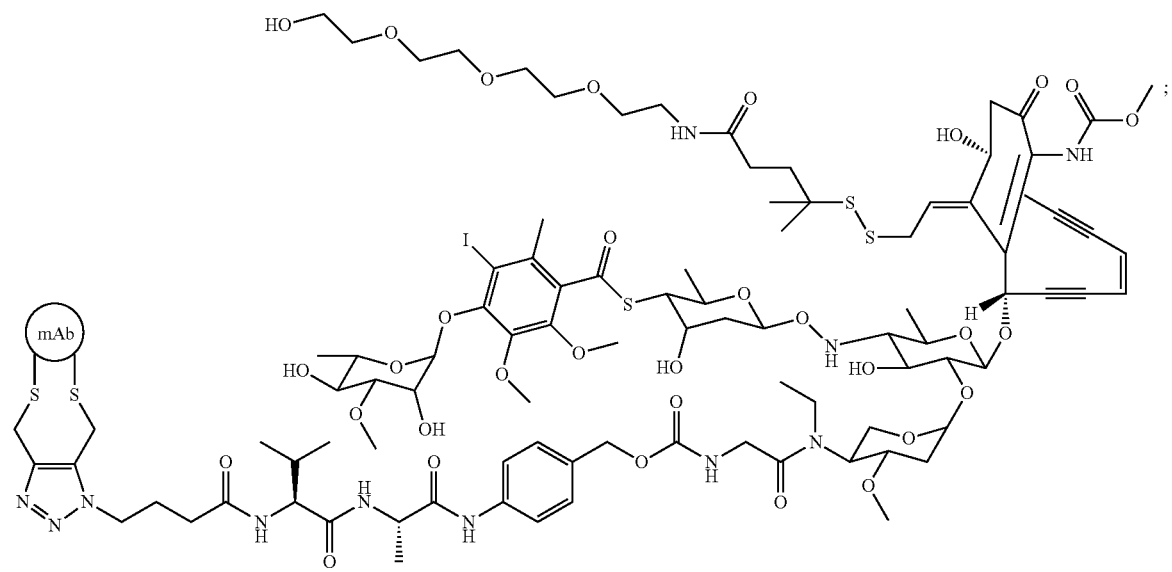

the structure of conjugate ZV0519 is shown as follows:

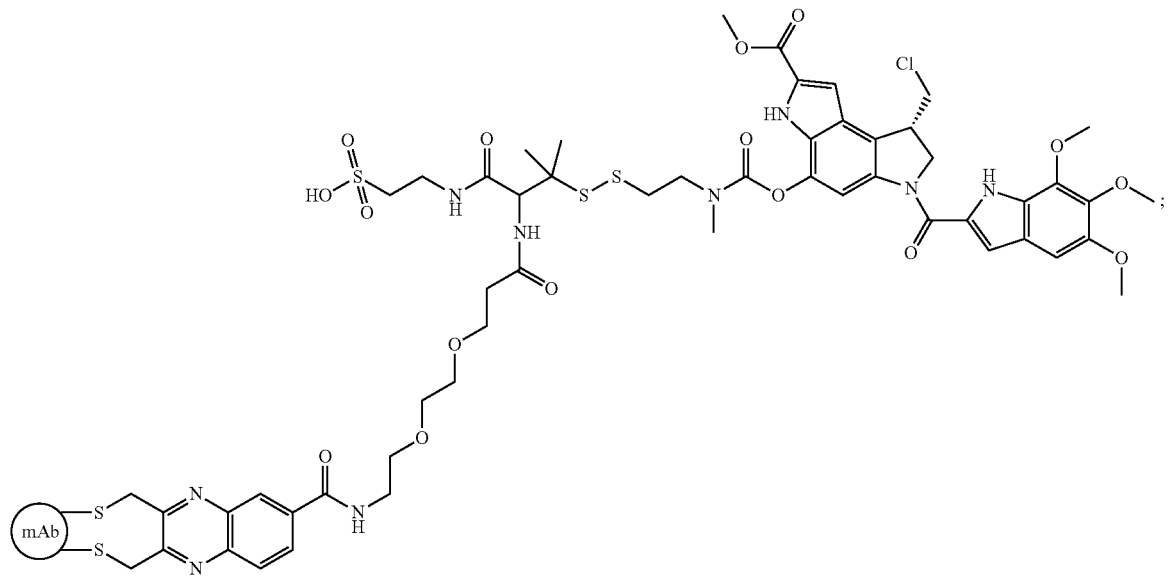

In the second aspect of the invention, it provides a pharmaceutical composition, which comprises: the antibody-drug conjugate according to the first aspect of the present invention, and a pharmaceutically acceptable carrier.

In the third aspect of the invention, it provides a use of the antibody-drug conjugate according to the first aspect of the present invention in preparing an anti-tumor medicine.

In another preferred embodiment, the tumor comprises 5T4 positive tumor, and preferably comprises breast cancer, gastric cancer, ovarian cancer, lung cancer and so on.

In the fourth aspect of the invention, it provides a method for treating or preventing a tumor, which comprises the step of administering to a subject in need thereof the antibody-drug conjugate according to the first aspect of the present invention; or the pharmaceutical composition according to the second aspect of the present invention.

In the fifth aspect of the invention, it provides a preparation method for the antibody-drug conjugate according to the first aspect of the present invention, which comprises the following steps:

configuring a reaction system which comprises an antibody and a free drug molecule, and then performing a coupling reaction to prepare the antibody-drug conjugate, wherein the drug molecule has a linker.

In another preferred embodiment, the reaction system has a pH from 6.5 to 8.0; preferably from 6.8 to 7.8; and more preferably from 7.0 to 7.5, such as 7.1, 7.2, 7.3, and 7.4.

In another preferred embodiment, the drug molecule is linked to a lysine (K) site in the light chain constant region of the antibody.

In another preferred embodiment, the reaction time is from 3 h to 16 h.

In another preferred embodiment, the molar ratio of the antibody to the drug molecule is from 1-2: 3-20; and preferably from 1: 6-10.

It should be understood that, within the scope of the present invention, the technical features specifically described above and below (such as in the Examples) can be combined with each other, thereby constituting a new or preferred technical solution which needs not be described one by one.

DETAILED DESCRIPTION OF THE INVENTION

Figure 1:
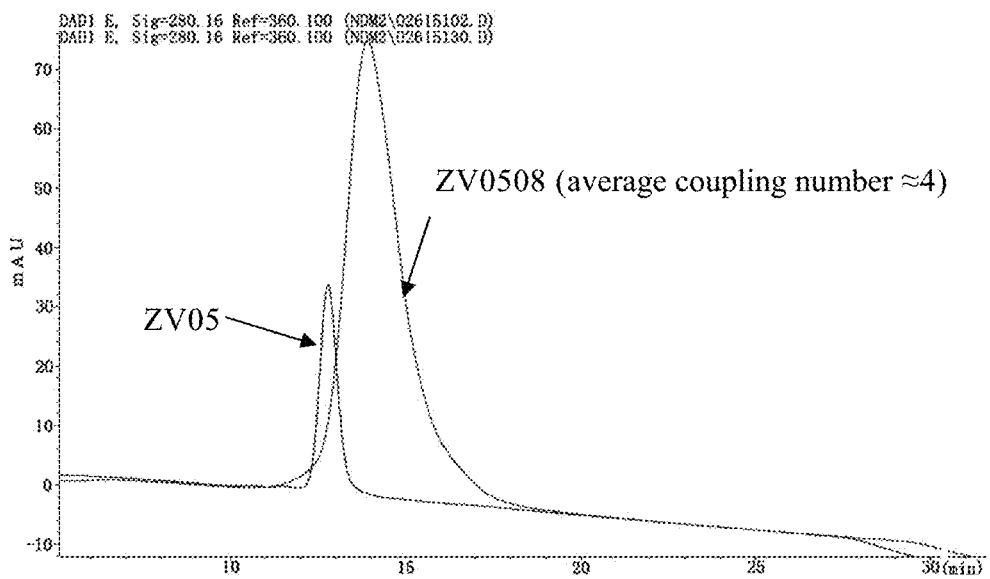
FIG. 1 shows the analysis results of HIC-HPLC analysis of ADC ZV0508.

Through extensive and intensive researches, the inventors have obtained an anti-5T4 antibody-drug conjugate which shows a significant anti-tumor effect. The invention also provides a use of the anti-5T4 antibody-drug conjugate in preparation of medicine and its application in inhibiting or preventing tumors.

In a preferred embodiment of the present invention, a humanized anti-5T4 monoclonal antibody (such as a ZV05 antibody) is used, which exhibits high affinity on both 5T4 antigen and tumor cells expressing 5T4 antigen, and has strong endocytosis on tumor cells expressing 5T4 antigen. In addition, compared with a non-human monoclonal antibody, the immunogenicity of this humanized antibody is lower, thereby avoiding the HAMA response and allowing high doses and repeated administration for a therapeutic response.

The antibody and small molecule drugs can be coupled using conventional coupling techniques in the art, such as the SeaGen ligation method. The antibody and the small molecule drug are preferably coupled by the method of the present invention, wherein the site-directed quantitative coupling of the antibody and the drug can be achieved by using simple chemistry and purification steps of the present invention, and the homogeneity of the conjugate is higher. Among a series of antibody drug conjugates provided by the present invention, ZV0508 exhibits a broader spectrum and superior in vivo antitumor activity.

The present invention uses a linker (L) moiety which is capable of coupling to a specific lysine position of the constant region of the antibody, or to a disulfide-reduced cysteine. After one-step hydrophobic purification (HIC), antibody-conjugated drugs with site-directed and quantitative coupling are obtained.

The antibody (Ab) is coupled to the drug moiety (D) via a linker (L, including L1 or L2) through a disulfide-reduced cysteine or a reactive lysine in the constant region to form an antibody-drug conjugate: Ab-(L-D)n, wherein n is 1-4. Coupling methods and therapeutic use of the antibody drug conjugates are disclosed in the present invention.

Before describing the present invention, it should be understood that the invention is not limited to the described particular methodology and experimental conditions, as such methods and conditions may be varied. It is also to be understood that the terminology used herein is only for the purpose of describing particular embodiments, and is not intended to be limiting, and the scope of the invention will be limited only by the appended claims.

Unless otherwise defined, all technical and scientific terms used herein have the same meaning as commonly understood by one having ordinary skill in the art to which this invention belongs. As used herein, the term "about" when used in reference to a particular listed value means that the value can vary from the listed value by no more than 1%. For example, as used herein, the expression of "about 100" includes all values between 99 and 101 (for example, 99.1, 99.2, 99.3, 99.4, etc.).

Although any methods and materials similar or equivalent to those described in this disclosure may be used in the practice or testing of the present invention, the preferred methods and materials are exemplified herein.

The present invention provides two types of coupling methods. Small molecules of toxin are coupled to an antibody through a specific linker, and the lethality of the antibody against tumor cells are greatly improved without changing the affinity of the antibody.

The term "antibody" or "immunoglobulin" as used herein refers to a heterotetrameric glycoprotein with the same structural feature of about 150,000 daltons, which consists of two identical light chains (L) and two identical heavy chains (H). Each light chain is linked to a heavy chain by a covalent disulfide bond, and the numbers of disulfide bonds between the heavy chains of different immunoglobulin isoforms are different. Each heavy and light chain also has regularly spaced intrachain disulfide bonds. Each heavy chain has a variable region (VH) at one end, followed by a plurality of constant regions. Each light chain has a variable region (VL) at one end and a constant region at the other end; the constant region of the light chain corresponds to the first constant region of the heavy chain; and the variable region of the light chain corresponds to the variable region of the heavy chain. An interface between the variable regions of the light and heavy chains is formed by particular amino acid residues.

As used herein, the term "variable" means that some certain portions of the variable region of an antibody differ in sequence and contribute to the binding and specificity of each particular antibody to its particular antigen. However, the variability is not evenly distributed throughout the antibody variable region. It is concentrated in three regions in the light and heavy chain variable regions called complementary determining regions (CDRs) or hypervariable regions. The relatively conserved portions of the variable regions are referred as framework regions (FRs). The variable regions of the natural heavy and light chains each comprises four FR regions, which are in a substantially β-folded configuration, and are linked by three CDRs that form the linker ring and, in some cases, form a partial β-folded structure. The CDRs in each chain stand close together through FR regions and form the antigen-binding site of the antibody together with the CDRs of the other chain (see Kabat et al., NIH Publ. No. 91-3242, Vol. I, 647-669 (1991)). Constant regions are not directly involved in the binding of the antibodies to the antigens, but they exhibit different effector functions, such as antibody-dependent cytotoxicity involved in antibodies.

The light chain of vertebrate antibody (immunoglobulin) can be divided into two distinct types (κ or λ) according to the amino acid sequences of constant region. Based on the amino acid sequences of heavy chain constant region, immunoglobulins could be divided into different species. There are five classes of immunoglobulins: IgA, IgD, IgE, IgG and IgM, and some of them can be further divided into subclass: IgG1, IgG2, IgG3, IgG4, IgA and IgA2. The heavy chain constant regions corresponding to different classes of immunoglobulins can be named as α, δ, ε, γ and μ. The subunit structures and 3D configurations of different immunoglobulins are well known to those skilled in the art.

In general, the antigen-binding properties of an antibody can be described by three specific regions located in the heavy chain and light chain variable region, referring as variable regions (CDRs), and this segment is separated into four framework regions (FRs). The sequences of four FRs amino acids are relatively conservative and do not directly participate in the binding reaction. A cyclic structure is formed by these CDRs, which are close to each other in the spatial structure through β-folds formed by the FRs between them. The CDRs on the heavy chains and the CDRs on the corresponding light chains constitute the antigen-binding site of the antibody. The amino acid sequence of the same type of antibody can be compared to determine which amino acids constitute the FR or CDR region.

The present invention includes not only intact antibodies but also fragments thereof or fusion proteins formed by antibodies with other sequences which have immunological activity. Accordingly, the present invention also includes fragments, derivatives and analogs of said antibodies.

As used herein, the terms "fragments", "derivatives" and "analogs" refer to the polypeptides that substantially maintain the same biological function or activity of the antibodies of the present invention. The polypeptide fragments, derivatives or analogs of the present invention may be (i) a polypeptide with one or more conservative or non-conservative amino acid residues (preferably the conservative amino acid residues) being substituted, while such a substituted amino acid residue may or may not be encoded by a genetic code, or (ii) a polypeptide having substituted group(s) in one or more amino acid residues, or (iii) a polypeptide formed by fusion of the mature polypeptide with another compound (such as the compound that prolongs the half life of the polypeptide, such as polyethylene glycol), or (iv) a polypeptide with additional amino acid sequence fused to said polypeptide sequence (such as fusion proteins formed by fusion with leader sequence, secretion sequence or sequence used to purify the polypeptide or proprotein sequence, or a fusion protein formed with a 6His tag. According to the teachings of the present application, these fragments, derivatives and analogs are within the scope commonly known by the skilled person.

In the present invention, the antibody of the present invention also includes the conserved variants thereof which refers to the polypeptides formed by substituting at most 10, preferably at most 8, more preferably at most 5, and most preferably 3 amino acid of the amino acid sequence of the polypeptide of the present invention with the amino acid having similar or analogous properties. These conservative variant polypeptides are preferably formed by carrying out the amino acid substitution according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The sequence of the DNA molecule of the antibody or fragment thereof of the present invention can be obtained by conventional techniques such as PCR amplification or genomic library screening. In addition, the coding sequences of the light and heavy chains can be fused together to form a single chain antibody.

Once the relevant sequence is obtained, the relevant sequence can be obtained in bulk using the recombination method. It is usually cloned into a vector, transferred to a cell, and then isolated from the host cell after proliferation by conventional methods.

In addition, artificial synthetic methods can be used to synthesize relevant sequences, especially when the length of the fragment is short. In general, a very long fragment can be obtained by first synthesizing multiple small fragments and then ligating them.

At present, DNA sequences encoding the antibody of the present invention (or fragments thereof, or derivatives thereof) can be completely obtained by chemical synthesis. Then the DNA sequence can be introduced into a variety of current DNA molecules (or vectors) and cells known in the art. In addition, mutations can also be introduced into the protein sequences of the present invention by chemical synthesis.

The present invention also relates to vectors comprising the suitable DNA sequence as described above and a suitable promoter or control sequence. These vectors can be used to transform suitable host cells to enable them to express proteins.

Host cells can be prokaryotic cells, such as bacterial cells; or lower eukaryotic cells, such as yeast cells; or higher eukaryotic cells, such as mammalian cells.

For example, the antibody of the present invention can be produced by the following method.

First, an expression vector comprising a nucleotide sequence encoding the antibody of the present invention and an expression regulatory sequence operably linked to the sequence is provided.

The term "expression regulatory sequence" as used herein generally refers to a sequence involved in the control of expression of a nucleotide sequence. Expression regulatory sequences include promoter and termination signals operably linked to a nucleotide sequence of interest. They usually also include the sequences required for proper translation of the nucleotide sequence. "Operably linked" means that portions of a linear DNA sequence are capable of affecting the activity of other portions of the same linear DNA sequence. For example, if a promoter or enhancer increases the transcription of a coding sequence, it is operably linked to the coding sequence.

DNA sequences encoding the monoclonal antibody of the present invention can be produced by conventional means well known to those skilled in the art. For example, a nucleotide sequence encoding the heavy chain variable region and the light chain variable region of the monoclonal antibody can be artificially synthesized or amplified by PCR according to the sequences disclosed in the present invention. These nucleotide sequences are then inserted into appropriate expression vectors by selection of appropriate cleavage sites using various methods well known in the art, and they are placed in front of the coding sequence of the heavy chain constant region and the coding sequence of the light chain constant region carried by expression vector (s), respectively and in the same reading frame. The expression vectors used in the present invention are various commercially available expression vectors known to those skilled in the art, such as pPIC9K.

Subsequently, an appropriate host cell is transformed with the expression vector obtained above. "Host cells" generally include prokaryotic cells and eukaryotic cells. Examples of commonly used prokaryotic host cells include *Escherichia coli, Bacillus subtilis* and the like. Commonly used eukaryotic host cells include yeast cells, insect cells, and mammalian cells. In the present invention, mammalian cells are preferred. Mammalian cell lines are usually used as host cells for expression of eukaryotic cell-derived polypeptides. Propagation of mammalian cells in culture is well known in the art. See "Tissue Culture", Academic Press, Kruse and Patterson ed. (1973), which is incorporated herein by reference. Preferred mammalian cells are a number of commercially available immortalized cell lines. These immortalized cell lines include, but are not limited to, Chinese hamster ovary (CHO) cells, Vero cells, HeLa cells, baby hamster kidney (BHK) cells, monkey kidney cells (COS), human hepatocyte cancer cells (such as Hep G2), and many other cell lines. They provide post-translational modifications to protein molecules, including correct folding, proper disulfide bond formation, and glycosylation at the correct site. Although in the following examples, the present invention exemplifies only examples in which CHO cells are used as host cells, those skilled in the art will recognize that the present invention can also employ the above cell lines by reading the detailed description and specific examples of the present invention.

There are many methods for transformation of host cells with expression vectors, and the transformation procedure used depends on the host to be transformed. Methods for introducing heterologous polynucleotides into mammalian cells are known in the art, which include dextran mediated transfection, calcium phosphate precipitation, Polybrene (1, 5-dimethyl-1, 5-diazaundecamethylene polymethobromide) mediated transfection, protoplast fusion, electroporation, liposome-mediated transfection, and direct microinjection of DNA into the nucleus. In the present invention, preferred methods are electroporation or liposome-mediated methods and the like. For example, a liposome assay kit from Invitrogen can be used to transfect host cells such as CHO cells.

The transformed host cells are then cultured under conditions suitable for expression of the antibody of the present invention. Then the antibody of the present invention are purified and obtained using conventional immunoglobulin purification steps such as protein A-Sepharose, hydroxyapatite chromatography, gel electrophoresis, dialysis, ion exchange chromatography, hydrophobic chromatography, molecular sieve chromatography or affinity chromatography, etc, which are conventional separation and purification means well known to those skilled in the art.

The obtained monoclonal antibodies can be identified by conventional means. For example, the binding specificity of a monoclonal antibody can be determined by immunoprecipitation or an in vitro binding assay such as radioimmunoassay (RIA) or enzyme-linked immunosorbent assay (ELISA). The binding affinity of a monoclonal antibody can be determined, for example, by Scatchard analysis of Munson et al, Anal. Biochem., 107: 220 (1980).

The antibody of the present invention can be expressed intracellularly, or on the cell membrane, or secreted out of the cell. If desired, recombinant proteins can be isolated and purified by various separation methods by utilizing their physical, chemical and other properties. These methods are well known to those skilled in the art. Examples of such methods include, but are not limited to, conventional renaturation treatments, treatment with a protein precipitant (salting-out method), centrifugation, penetration-breaking bacteria, sonication, ultracentrifugation, molecular sieve chromatography (gel filtration), adsorption chromatography, ion-exchange chromatography, high performance liquid chromatography (HPLC) and various other liquid chromatography techniques, and combinations thereof.

In a preferred embodiment of the invention, the heavy chain variable region of the anti-5T4 antibody comprises three complementary determining regions:

CDR1:
(SEQ ID NO.: 1)
GFTFSSYE

CDR2:
(SEQ ID NO.: 2)
ISSSGSTI
and

CDR3:
(SEQ ID NO.: 3)
AREMQFGWELLGAFDI.

In a preferred embodiment of the invention, the light chain variable region of the anti-5T4 antibody comprises three complementary determining regions:

CDR1':
(SEQ ID NO.: 4)
QSVSSSY

CDR2':
(SEQ ID NO.: 5)
GAS
and

CDR3':
(SEQ ID NO.: 6)
QQYGSS.

In a preferred embodiment of the invention, the amino acid sequence of the heavy chain variable region of the anti-5T4 antibody is as follows:

(SEQ ID NO. 7)
MDWTWRFLFVVAAATGVQSQVQLVQSGGGLVQPGGSLRLSCAASGFTFSSY
EMNWVRQAPGKGLEWVSYISSSGSTIYYADSVKGRFTISRDNAKNSLYLQM
NSLRAEDTAVYYCAREMQFGWELLGAFDIWGQGTMVTVSS.

In a preferred embodiment of the invention, the amino acid sequence of the light chain variable region of the anti-5T4 antibody is as follows:

(SEQ ID NO. 8)
MDMRVPAQLLGLLLLWLSGARCEIVLTQSPGTLSLSPGERATLSCRASQSV
SSSYLAWYQQKPGQAPRLLIYGASSRATGIPDRFSGSGSGTDFTLTISRLE
PEDFAVYYCQQYGSSFGQGTKLEIK.

In a preferred embodiment of the invention, the amino acid sequence of the heavy chain variable region of the anti-5T4 antibody is as follows:

(SEQ ID NO. 9)
MDWTWRFLFVVAAATGVQSQVQLVQSGGGLVQPGGSLRLSCAASGFTFSSY
EMNWVRQAPGKGLEWVSYISSSGSTIYYADSVKGRFTISRDNAKNSLYLQM
NSLRAEDTAVYYCAREMQFGWELLGAFDIWGQGTMVTVSSASTKGPSVFPL
APSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCP
APELLGGPSVFLEPPKPKDTLMISRTPEVTCVVVDVSHEDPEVKFNWYVDG
VEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHN
HYTQKSLSLSPGK.

In a preferred embodiment of the invention, the amino acid sequence of the light chain variable region of the anti-5T4 antibody is as follows:

(SEQ ID NO. 10)
MDMRVPAQLLGLLLLWLSGARCEIVLTQSPGTLSLSPGERATLSCRASQSV
SSSYLAWYQQKPGQAPRLLIYGASSRATGIPDRFSGSGSGTDFTLTISRLE
PEDFAVYYCQQYGSSFGQGTKLEIKRTVAAPSVFIFPPSDEQLKSGTASVV
CLLNNFYPREAKVQWKVDNALQSGNSQESVTEQDSKDSTYSLSSTLTLSKA
DYEKHKVYACEVTHQGLSSPVTKSFNRGEC.

In a preferred embodiment of the invention, the structure of the antibody-drug conjugate is as shown in formula II:

Ab-(L-D)n      II wherein:

Ab is an antibody;

D is a small molecule drug that inhibits tumor cells;

L is a linker connecting the antibody and the drug.

In another preferred embodiment, n is from 1 to 8, preferably n is an integer.

In another preferred embodiment, D is selected from the group consisting of:

Duostatin 5:
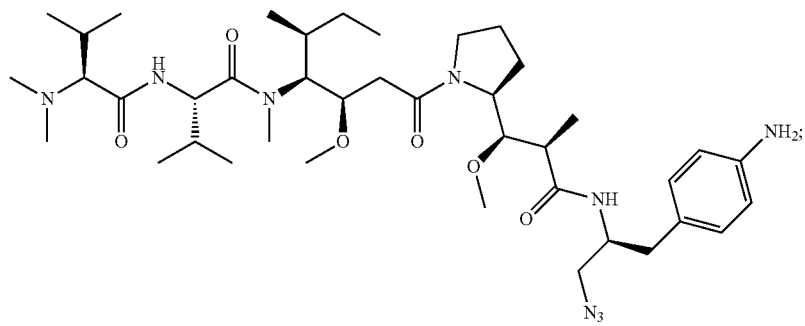 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(N)cc1)OC)N(C)C(=O)[C@@H](NC(=O)[C@H](C(C)C)N(C)C)C(C)C]
MMAF:
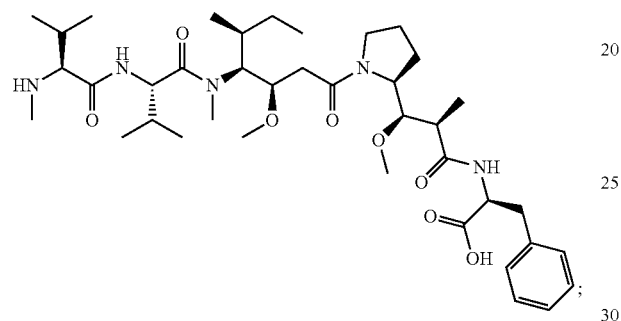
Duostatin 14:
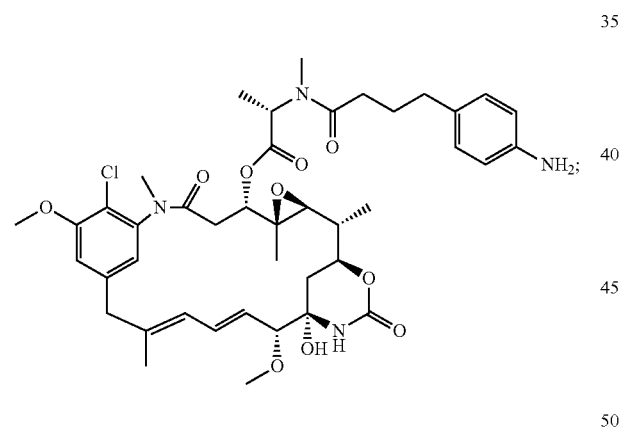
Duomycin 2:
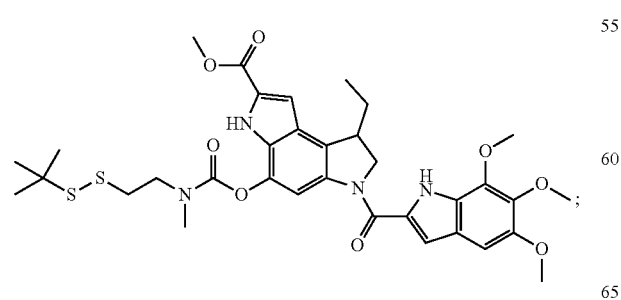

Duomycin 4:

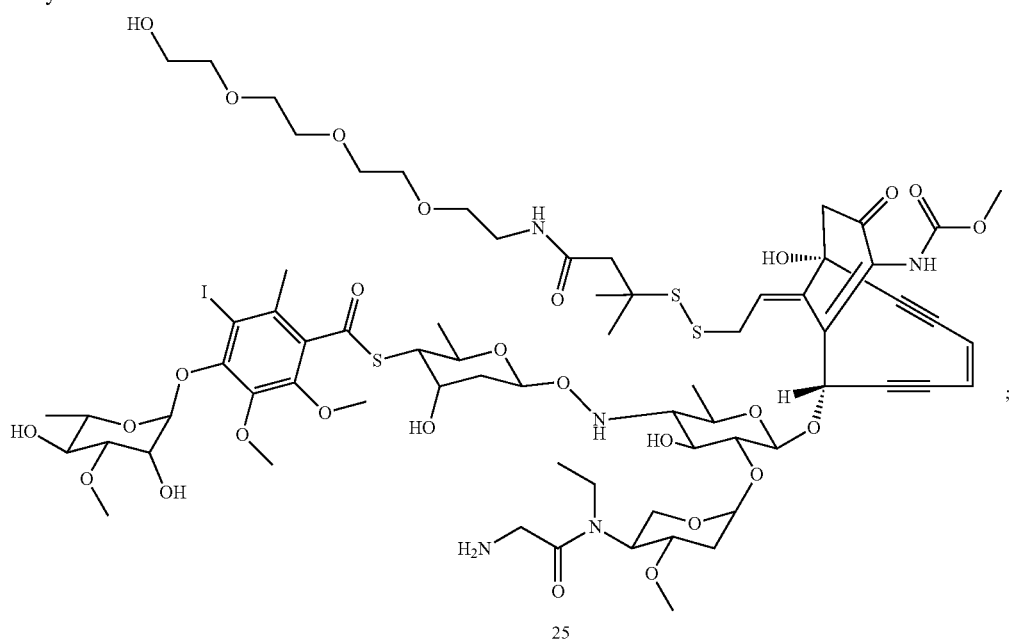

Calicheamicin•γ1:

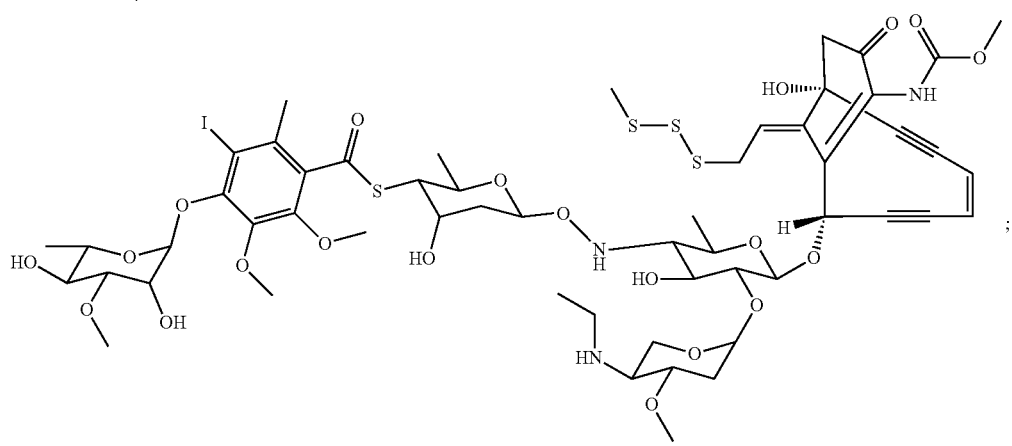

α-Amanitine:

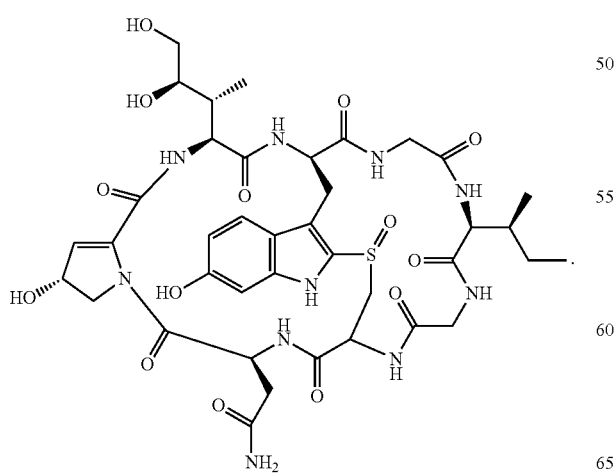

In a preferred embodiment of the invention, the structure of the antibody-drug conjugate is as shown in formula IV (that is, L includes $L^1$—$L^2$):

$$Ab\text{-}(\text{-}L^1\text{—}L^2\text{—}D)_n \qquad \qquad IV$$

in formula IV, the structure of $L^1$—$L^2$ is selected from

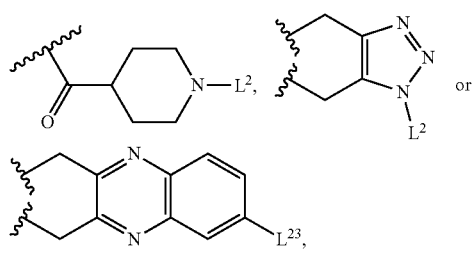

wherein $L^2$ is a linker selected from the group consisting of —$(CH_2)n$-, —$(CH_2CH_2O)n$-, Val-Cit, Ala-Ala-Asn, and a combination thereof;

Ab, D, n are as described above;
the wavy line indicates the connection position with antibody.
In another preferred embodiment, the antibody-drug conjugate is selected from the group consisting of:
ZV0508, ZV0512, ZV0513, ZV0501, ZV0503, ZV0504, ZV0517, ZV0518, ZV0505, ZV0516, ZV0515, ZV0519;
wherein the structure of conjugate ZV0508 is shown as follows:
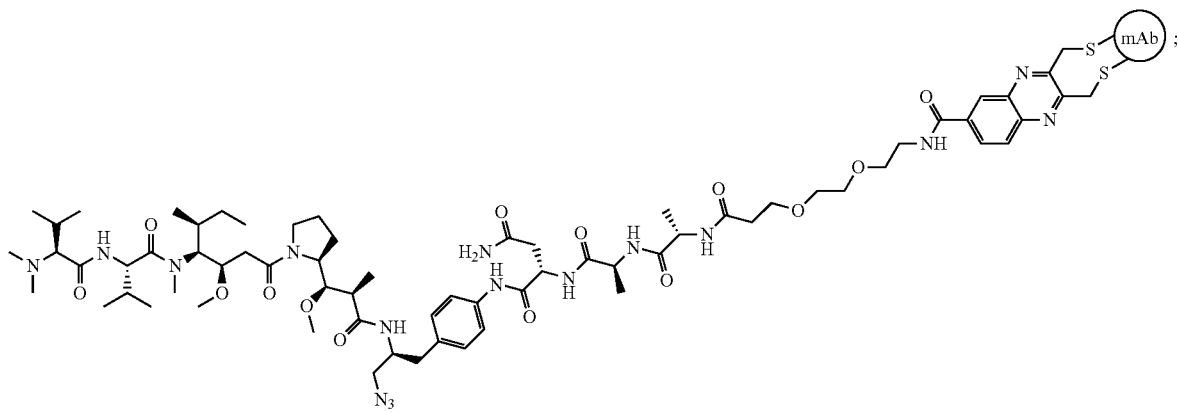
the structure of conjugate ZV0512 is shown as follows:
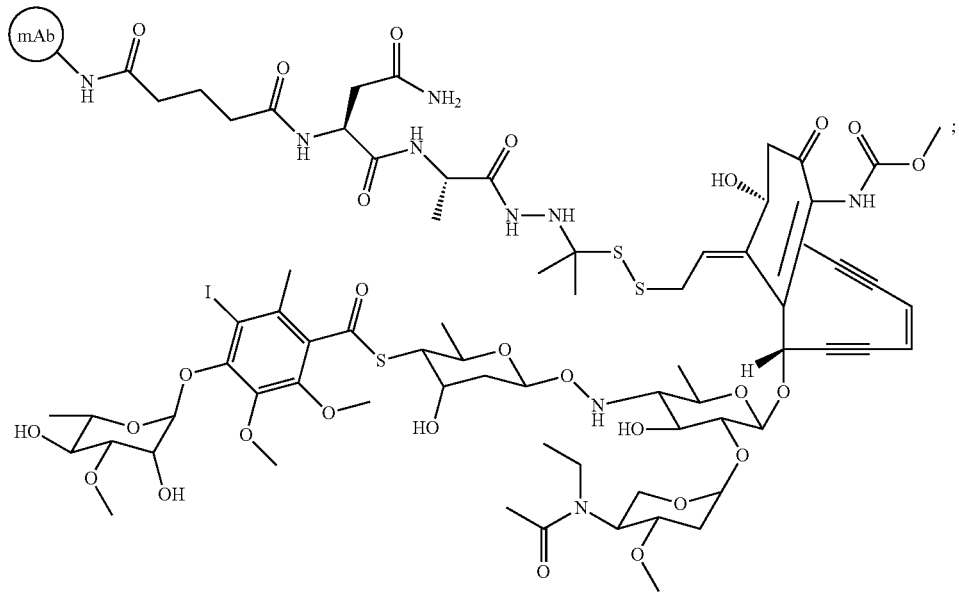

the structure of conjugate ZV0512 is shown as follows:
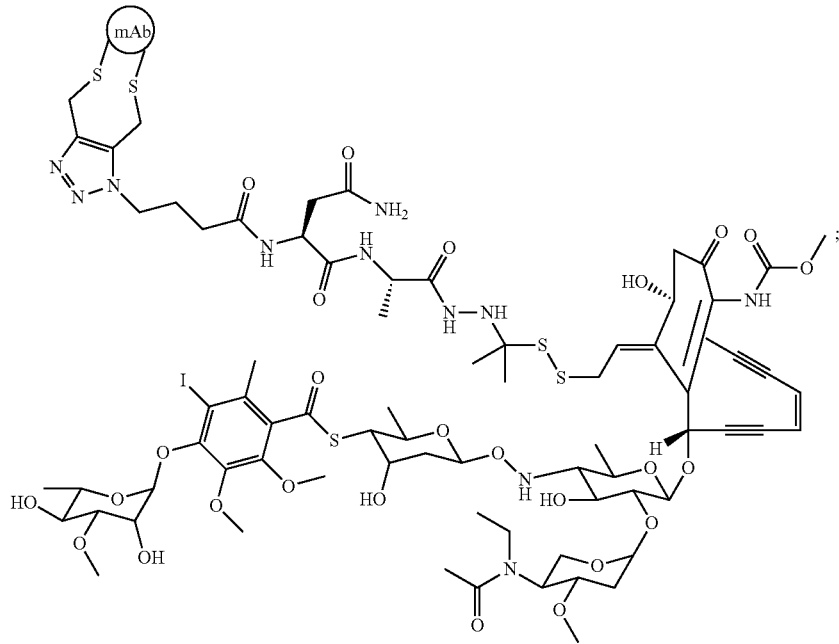
the structure of conjugate ZV0501 is shown as follows:
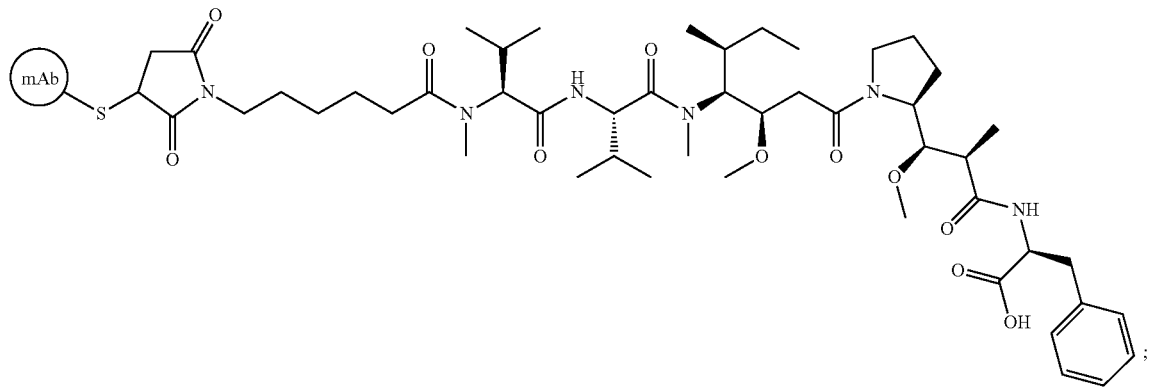 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)CC(SC)C1=O)C(C)C]
the structure of conjugate ZV0503 is shown as follows:
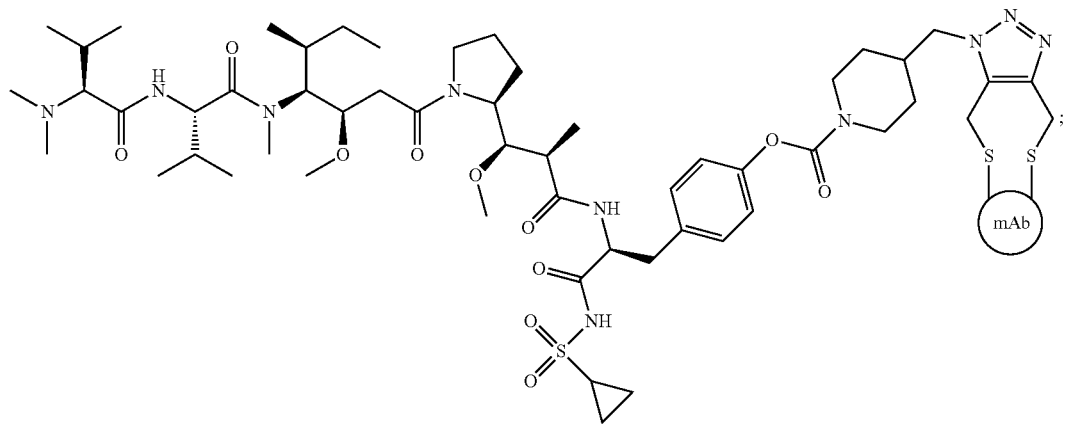 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(Cn3nnc(CSC)c3CSC)CC2)cc1)C(=O)NS(=O)(=O)C1CC1)OC)N(C)C(=O)[C@@H](NC(=O)[C@H](C(C)C)N(C)C)C(C)C]

the structure of conjugate ZV0504 is shown as follows:
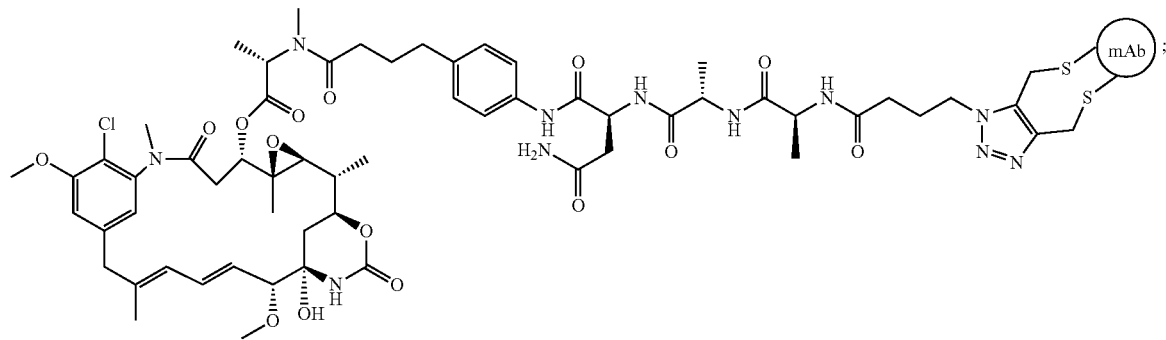
the structure of conjugate ZV0517 is shown as follows:
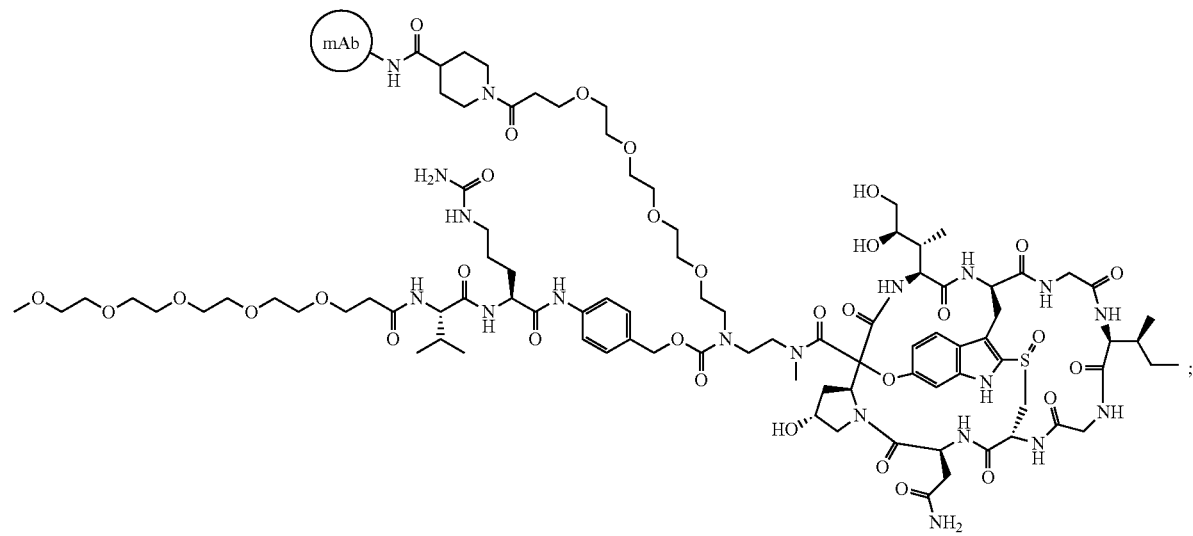 [SMILES: CC[C@H](C)[C@@H]1NC(=O)CNC(=O)[C@H]2Cc3c4[nH]c5cc(ccc35)OC(C(=O)N(C)CCN(CCOCCOCCOCCOCCC(=O)N3CCC(C(=O)NC)CC3)C(=O)OCc3ccc(NC(=O)[C@H](CCCNC(N)=O)NC(=O)[C@@H](NC(=O)CCOCCOCCOCCOCCOC)C(C)C)cc3)(C(=O)N[C@@H]([C@@H](C)[C@@H](O)CO)C(=O)N2)[C@@H]2C[C@@H](O)CN2C(=O)[C@H](CC(N)=O)NC(=O)[C@H](CS4=O)NC(=O)CNC1=O]
the structure of conjugate ZV0518 is shown as follows:
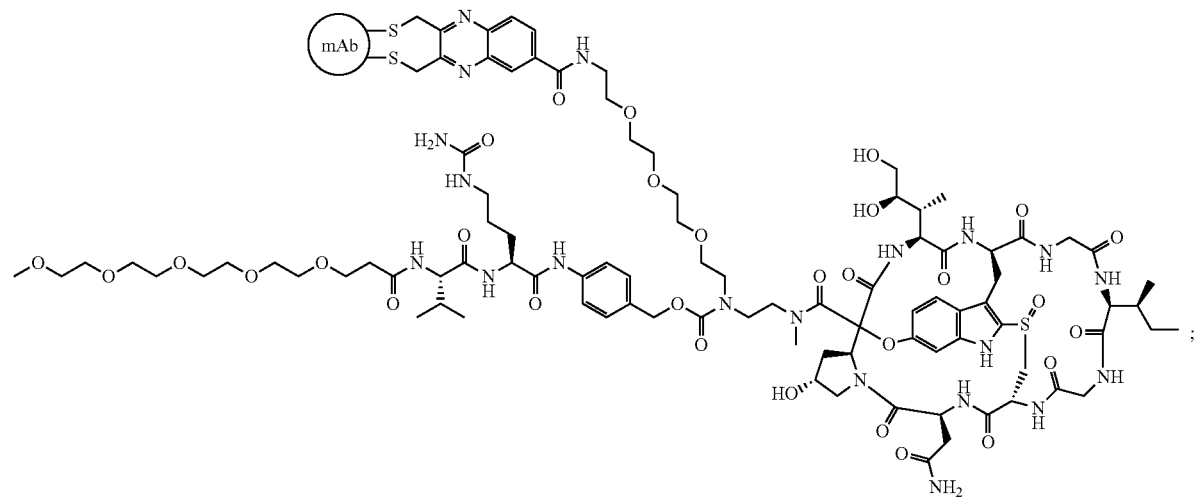 [SMILES: CC[C@H](C)[C@@H]1NC(=O)CNC(=O)[C@H]2Cc3c4[nH]c5cc(ccc35)OC(C(=O)N(C)CCN(CCOCCOCCOCCNC(=O)c3ccc5nc(CSC)c(CSC)nc5c3)C(=O)OCc3ccc(NC(=O)[C@H](CCCNC(N)=O)NC(=O)[C@@H](NC(=O)CCOCCOCCOCCOCCOC)C(C)C)cc3)(C(=O)N[C@@H]([C@@H](C)[C@@H](O)CO)C(=O)N2)[C@@H]2C[C@@H](O)CN2C(=O)[C@H](CC(N)=O)NC(=O)[C@H](CS4=O)NC(=O)CNC1=O]

the structure of conjugate ZV0505 is shown as follows:
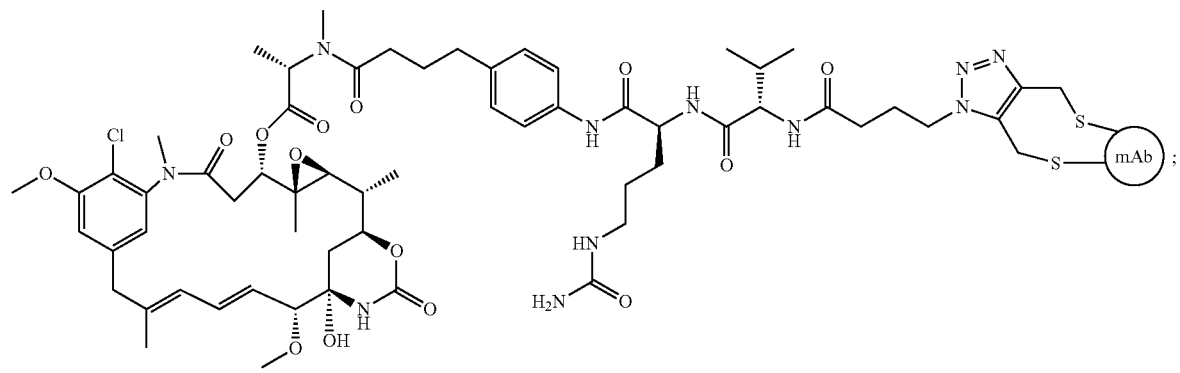
the structure of conjugate ZV0516 is shown as follows:
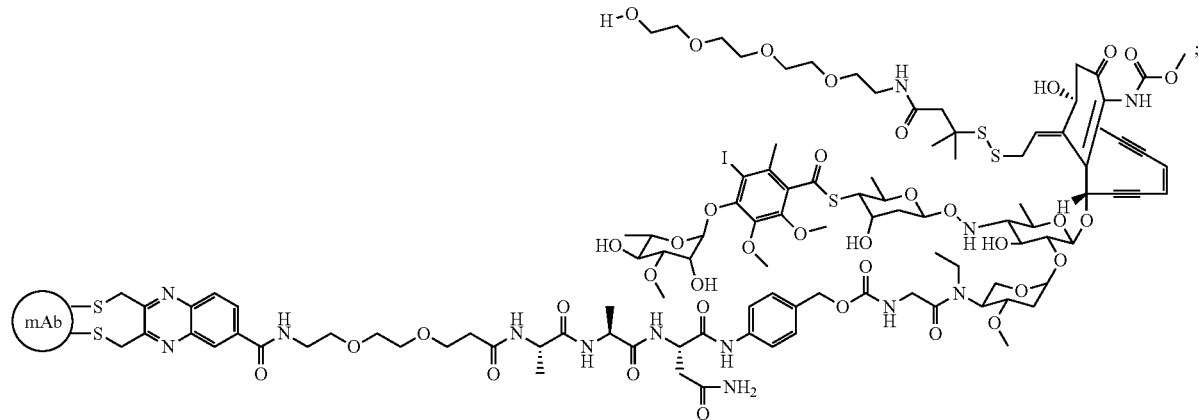
the structure of conjugate ZV0515 is shown as follows:
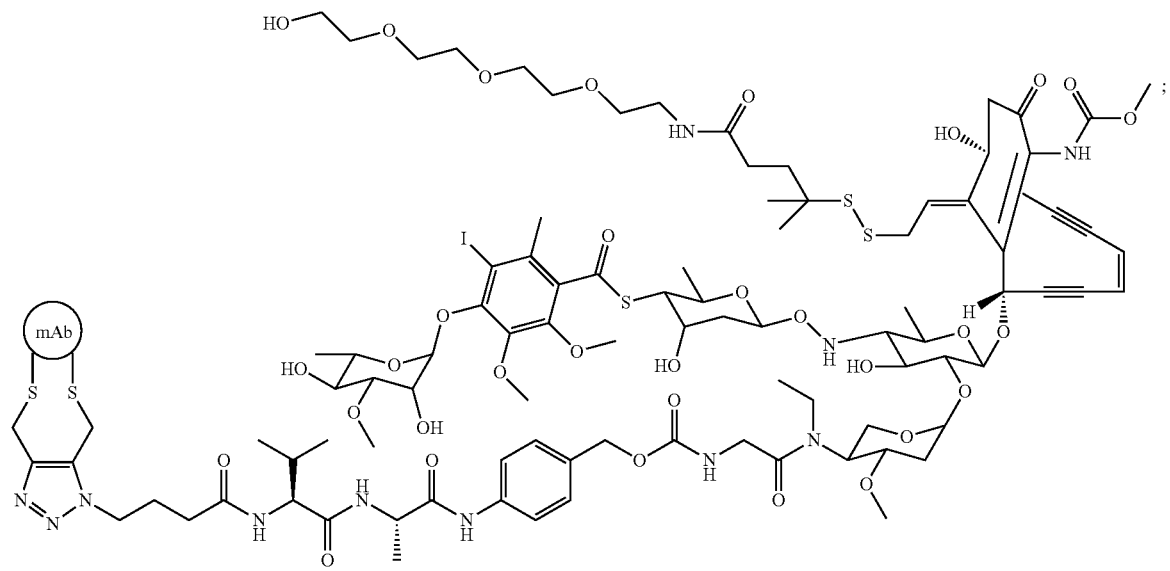

the structure of conjugate ZV0519 is shown as follows:

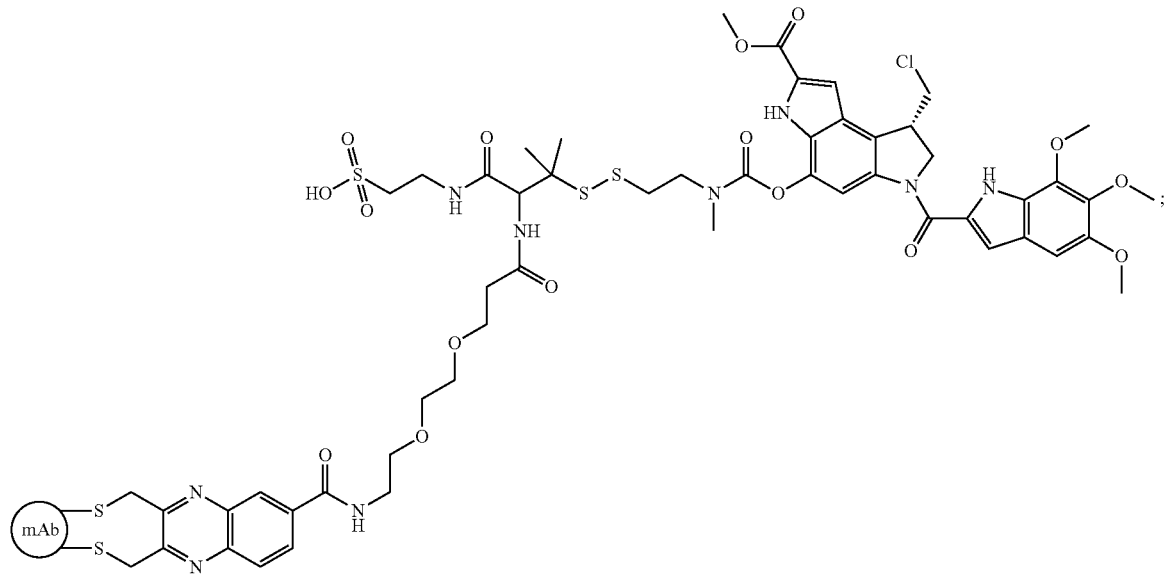

In another preferred embodiment, the coupling method for preparing the antibody-drug conjugate of the present invention includes two coupling modes, i.e., K-Lock and C-Lock. In the K-Lock coupling mode, the drug molecule is coupled to a lysine (K) residue in the antibody sequence. In the C-Lock coupling mode, the drug molecule is coupled to a cysteine (C) residue in the antibody sequence. The coupling method of the antibody-drug conjugate of the present invention is summarized below.

K-Lock method: The antibody can be directly linked to L1-D in a mild solution system. For example, 6-10 fold excess of L1-D reacts with antibody for 3-16 h at room temperature. Excess small molecule L1-D is removed by ultrafiltration. The antibody-drug conjugates are loaded onto a hydrophobic chromatography column (HIC), and anti-5T4 antibody-drug conjugates with a coupling number of 2 are purified and obtained.

C-Lock method: After TCEP reduction, the antibody is directly linked to L2-D in a mild solution system. For example, the antibody is reduced with a 5-10 fold excess of TCEP at room temperature and excess TCEP is removed by ultrafiltration. 5-10 fold of L2-D is added into the reduced antibody solution for reaction, and excess small molecule L2-D is removed by ultrafiltration. The antibody-drug conjugates are loaded onto a hydrophobic chromatography column (HIC), and anti-5T4 antibody-drug conjugates with a coupling number of 4 are purified and obtained.

Use of the antibody-drug conjugate in the preparation of anti-tumor medicine is also provided in the present invention.

The anti-tumor medicine comprises an effective amount of the antibody-drug conjugate according to the present invention, and at least one pharmaceutically acceptable carrier, diluent or excipient. For preparation, the active ingredient is usually mixed with an excipient, or diluted with an excipient, or enclosed in a carrier which may be in the form of capsule or sachet. When the excipient acts as a diluent, solid, semi-solid or liquid materials can be used as media for an excipient, carrier and ingredient. Thus, the composition may be a tablet, a pill, a powder, a solution, a syrup, a sterile injectable solution or the like.

Suitable excipients include lactose, glucose, sucrose, sorbitol, mannitol, starch, microcrystalline cellulose, polyvinylpyrrolidone, cellulose, water, and the like. Preparations may also include wetting agent, emulsifier, preservative (such as methyl and propyl hydroxybenzoate), sweetener, and the like. The anti-tumor medicine can be formulated in a unit or multi-dose form. Each dosage form comprises a calculated and predetermined amount of the anti-5T4 antibody-Dolastatin conjugate to produce desired therapeutic effect, as well as suitable pharmaceutical excipients.

The anti-tumor medicine can be administered by conventional routes including, but not limited to, intramuscular, intraperitoneal, intravenous, subcutaneous, intradermal, topical administration and the like.

When the pharmaceutical composition is used, a safe and effective amount of the antibody-drug conjugate is administered to a human wherein the safe effective amount is preferably in the range of 0.5 to 50 micrograms per kilogram of body weight, more preferably 1 to 10 micrograms per kilogram of body weight. Of course, the route of administration, the patient's health status and other factors, should be considered for the specific dose, which are within the scope of skills of skilled practitioners.

In addition, the conjugates of the present invention may also be used in combination with other therapeutic agents, including but not limited to: various cytokines such as TNF, IFN, IL-2, etc.; various tumor chemotherapy medicine, such as 5-FU, methotrexate and other medicine that affect nucleic acid biosynthesis; alkylating agents such as nitrogen mustard and cyclophosphamide; medicines such as doxorubicin and actinomycin D that interfere with transcriptional processes to prevent RNA synthesis; medicines (such as vincristine, camptothecin classes etc.) that affect protein synthesis and certain hormone medicines, and so on.

Compared with prior arts, the beneficial effects of the present invention include:

(1) The 5T4-targeted antibody drug conjugate of the present invention has a significant anti-tumor effect;

(2) The antibody-drug conjugate of the present invention exhibits high affinity on both 5T4 antigen and tumor cells expressing 5T4 antigen, and has strong endocytosis on tumor cells expressing 5T4 antigen.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook et al., Molecular Cloning Laboratory Guide (New York: Cold Spring Harbor Laboratory Press, 1989), or according to the manufacture's instructions. Unless indicated otherwise, all percentage and parts are calculated by weight. Unless otherwise stated, the experimental materials and reagents used in the following examples are commercially available.

General synthesis step A method for synthesizing an active ester from a compound having a carboxyl group (such as NHS)

A carboxyl compound was dissolved in dichloromethane or N, N-dimethylformamide. 1.5 equivalents of N-hydroxysuccinimide and 1.5 equivalents of EDCI were added. The reaction solution was stirred at room temperature for 1 hour until the carboxyl compound was consumed completely. The progress of the reaction was monitored by RP-HPLC. The reaction solution was then diluted with dichloromethane, and organic phase was washed with citric acid (aq. 10%) and saturated brine. The organic phase was separated and dried, and purified by HPLC or medium pressure normal phase silica gel chromatography, so as to give the corresponding active ester.

The amino acid sequence of heavy chain of the control antibody (humanized A1 antibody) used in the examples is as follows:

(SEQ ID NO. 11)
EVQLVESGGGLVQPGGSLRLSCAASGYTFTNFGMNWVRQAPGKGLEWVAWI

NTNTGEPRYAEEFKGRFTISRDNAKNSLYLQMNSLRAEDTAVYYCARDWDG

-continued
AYFFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFL

YSKLTVDKSRWQQGNVFSCSVMHEALHNHYTQKSLSLSPGK;

The acid sequence of the light chain amino of the control antibody is as follows:

(SEQ ID NO. 12)
DIQMTQSPSSLSASVGDRVTITCKASQSVSNDVAWYQQKPGKAPKLLIYFA

TNRYTGVPSRFSGSGYGTDFTLTISSLQPEDFATYYCQQDYSSPWTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

Example 1 Synthesis of Small Molecule Drugs

Synthesis Route of Small Molecule of Calicheamicin:

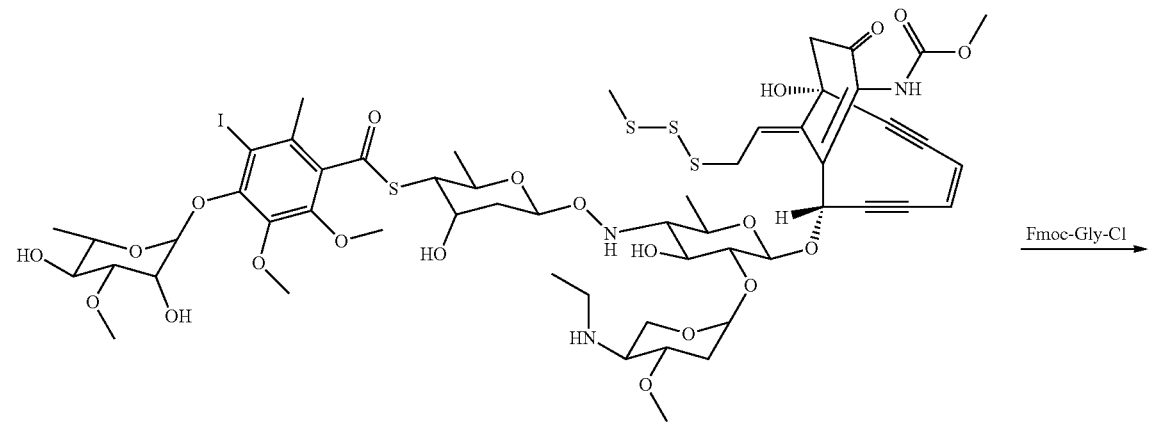

1

-continued
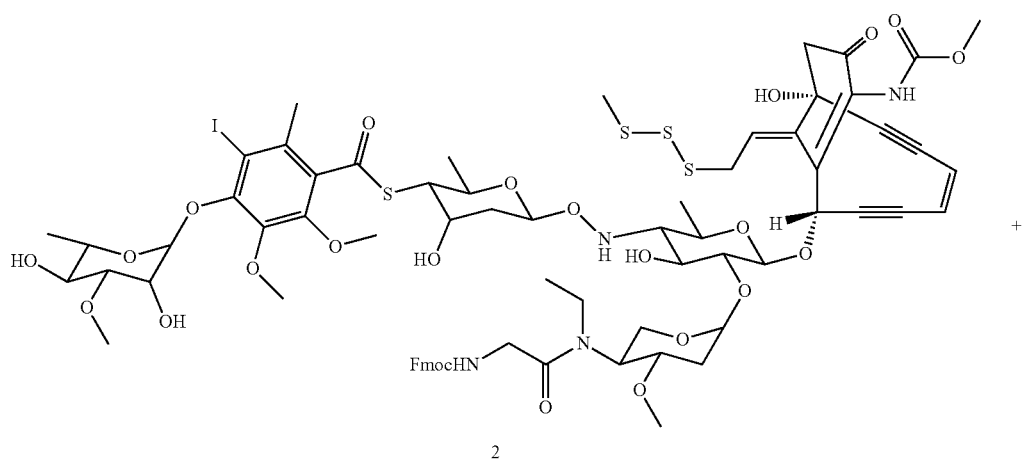
2
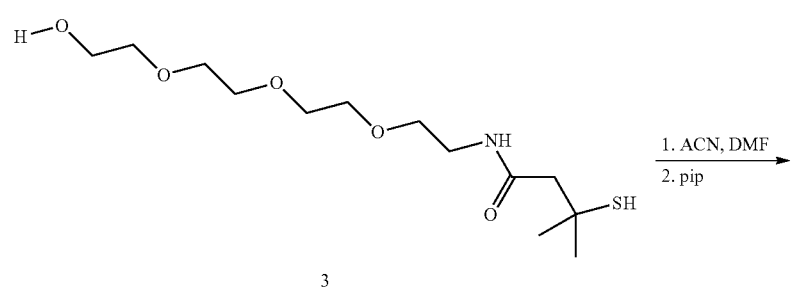
3
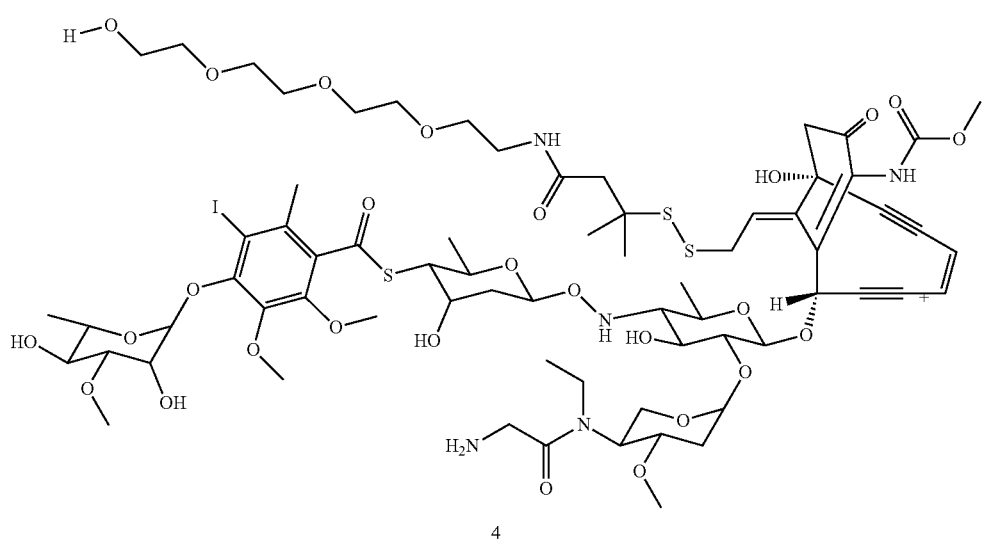
4
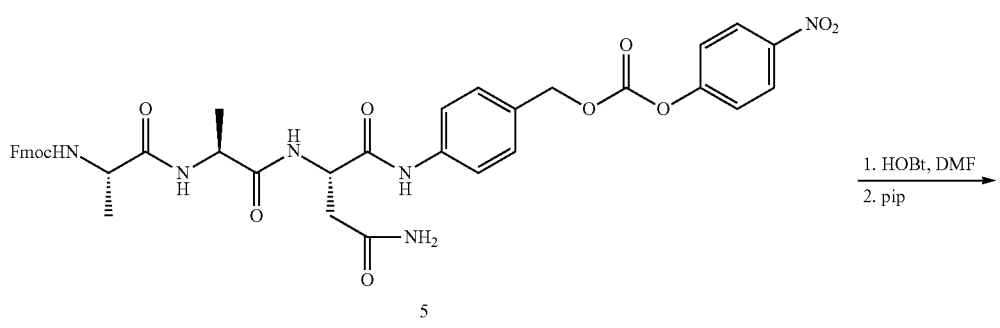
5

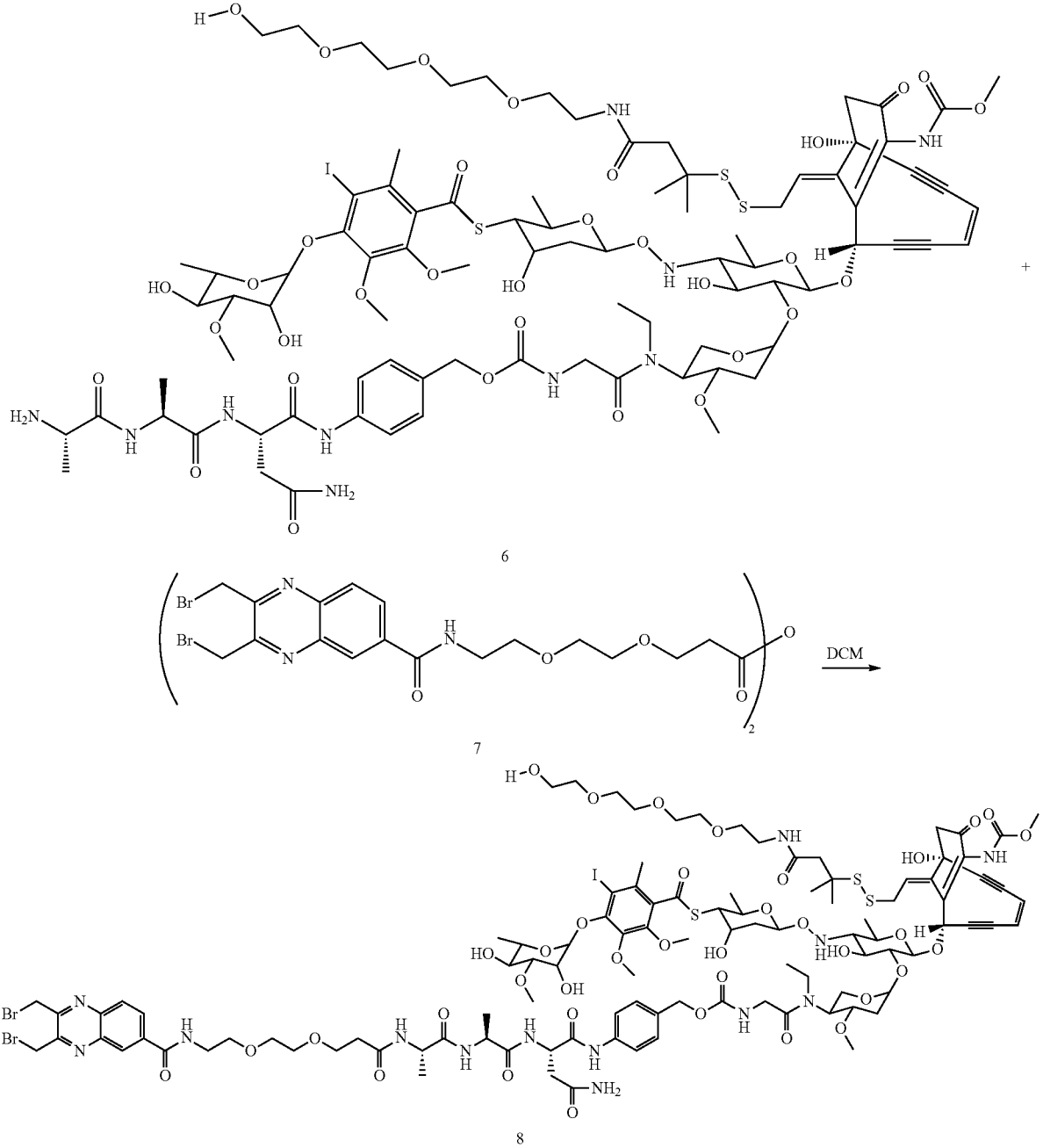

(9H-fluoren-9-yl)methyl (2-chloro-2-oxoethyl)carbamate (256 mg, 0.81 mmol) and diisopropylethylamine (DIEA, 173 μL, 1 mmol) were added to Khakime γ1 (1880 mg, 0.54 mmol, dissolved in 25 mL DMF). The mixture was stirred for 2 hours, then the solution was removed and purified by HPLC to obtain compound 2 (300 mg). MS m/z 1647.3 (M+H).

Synthesis of Compound 8:

Compound 2 (100 mg, 0.06 mmol) was dissolved in 4 mL of acetonitrile and 0.3 mL of DMF. Then Compound 3 (75 mg, 0.24 mmol) were added. After stirred for 16 hrs, 120 μL piperidine was added. After 30 min, the reaction solution was purified by HPLC to obtain compound 4 (60 mg, 60%). MS m/z 1654.4 (M+H).

Compound 5 (11 mg, 14 umol), N-Hydroxybenzotriazole (HOBt, 2 mg) and 5 μL, of diisopropylethylamine (DIEA) were added into into a solution of Compound 4 (20 mg, 12 umol, dissolved in 2 mL of DMF). The reaction mixture was stirred for one hour and then 40 μl, of piperidine was added. After 10 minutes, the mixture was purified by HPLC to obtain compound 6 (21 mg). MS m/z 2059.6(M+H).

Compound 7 (13 mg, 13 umol) and 3 μL of diisopropylethylamine (DIEA) were added into a solution of Compound 6 (21 mg, 10 umol, dissolved in 2 mL of Dichloromethane DCM). After stirring the reaction mixture for 20 minutes, the solvent was removed and Compound 8 (11 mg) was obtained via HPLC purification. MS m/z 2558.6(M+H).

Synthesis Route of Small Molecule of Duostatin5:

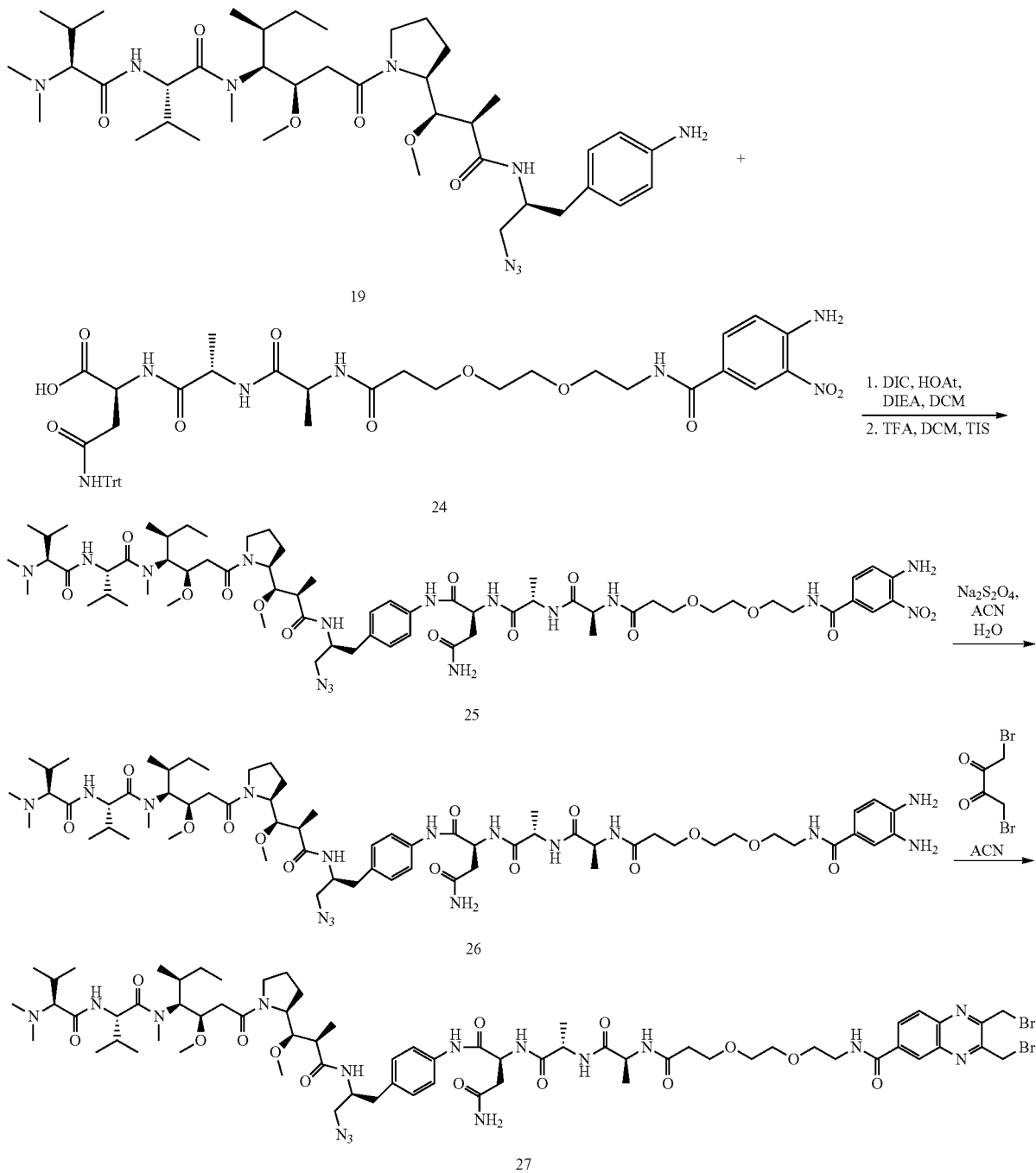

Synthesis of Compound 25:

TFA salt of compound 19 (1 mmol), Compound 24 (1 eq.), HOAt (3 eq.), dichloromethane or DCM (20 mL), diisopropylethylamine (DIEA 6 eq.) and DIC (2 eq.) were placed in a round bottom bottle. After stirring for 16 hours, the reaction solution was diluted with 20 mL of DCM and washed with 20 mL of water. After the organic phase was dried over sodium sulfate, the solvent was removed under reduced pressure, and the obtained glassy solid was directly used for the next reaction. The obtained solid was dissolved in 10 mL of DCM, 10 mL of trifluoroacetic acid (TFA) and 1 mL of triisopropylsilane and stirred for one hour. After the solvent was removed in vacuo, compound 6 was obtained via HPLC purification. MS m/z 1351.5 (M+H).

Synthesis of Compound 26:

Compound 25 (0.5 mmol), 20 mL of acetonitrile, 5 mL of water and 10 mL saturated NaHCO₃ aqueous solution were placed in a round bottom bottle. Then Na₂S₂O₄ (4 eq.) was added and the mixture was stirred for 20 min. Compound 7 was obtained via HPLC purification. MS m/z 1321.7 (M+H).

Synthesis of Compound 27:

Compound 26 (0.4 mmol) was dissolved in 10 mL of acetonitrile and 1, 4-dibromo-2, 3-butanedione (3 eq.) was added. After stirring for 20 min, Compound 27 was obtained via HPLC purification. MS m/z 1527.6 (M+H).

Example 2 Synthesis of Antibody

The variable region gene sequences of the heavy and light chains of the antibody (anti-5T4 antibody and control antibody A1) were obtained by chemical synthesis, and the constant region gene sequences of the heavy and light chains of the obtained antibody (anti-5T4 antibody and control antibody A1) were amplified by PCR. The variable region and the constant region of the heavy chain were assembled into an expression vector by restriction enzyme ligation; the variable region and the constant region of the light chain were assembled into another expression vector by a similar method. The heavy chain variable region and constant region expression vectors and the light chain variable region and constant region expression vectors were assembled together by enzyme ligation to obtain a recombinant expression vector for the antibody. The expression vector of the antibody was transformed into CHO cells for expression. The expression supernatant was collected, purified by protein A to obtain a high purity antibody, and the antibody was exchanged into a buffer system suitable for coupling via ultrafiltration or desalting column.

The 5T4-antibody was reduced with 15 fold of molar equivalents of TCEP (prepared in water) in C-Lock buffer (50 mM sodium phosphate, 4 mM EDTA, pH 7.0) for 3 hours at 37° C. or overnight at room temperature.

The fully reduced antibody was purified by buffer exchange through a PD-10 gel filtration column or by an Amicon rotary concentrator so that TCEP was removed.

The absorbance at 412 nm and 280 nm was measured using a spectrophotometer to quantify the free thiol in the antibody. About 6 free thiols should be produced from 3 disulfide bonds. After TCEP removal, the antibody concentration was quantified using a spectrophotometer based on 280 nm absorbance.

Example 3 Preparation of Anti-5T4 Antibody-Drug Conjugate

The corresponding drug was coupled to the antibody by using coupling methods such as K-Lock method or C-Lock method, thereby forming the ADCs listed in Table 1.

The K-Lock method. ZV0512 was taken as an example. An antibody (such as that having the light chain as shown in SEQ ID NO:10 and the heavy chain as shown in SEQ ID NO: 9) could be directly connected with drug molecule in a mild solution system.

At room temperature 25° C. (ranging from 4 to 37° C.), into 10 mg/ml of antibody (dissolved in phosphate buffer PBS. Concentration range was 5-30 mg/ml), 6-10 fold molar amount of drug molecule (dissolved in DMA and the volume was less than 10% of PBS) was added. After incubating for 3-16 h, the excess drug molecule was removed by ultrafiltration. The antibody-drug conjugates were loaded onto a hydrophobic chromatography column (HIC), equilibrated with 0.75-1M ammonium sulfate solution, and then eluted with 25 mM ammonium sulfate solution. The eluates containing ADCs with coupling number of 2 were combined, PBS was used for fluid replacement and anti-5T4 antibody-drug conjugates with coupling number of 2 were obtained.

The inventors have found that pH has a significant effect on the coupling reaction during the coupling process of antibody and the drug. Preferably, the pH of coupling is from 6.5 to 8.0; preferably, the pH of coupling is from 6.8 to 7.8; and more preferably, the pH of coupling is from 7.0-7.5, such as 7.1, 7.2, 7.3, and 7.4.

The experimental results showed that the antibody was almost not coupled with drug molecule at a pH less than 6. At pH 7.8, partial unreacted antibodies still remained and ADCs with a DAR number of 1 were in a major portion. When the pH was about 7.0, the main portion was ADCs with a DAR number of 2. Therefore, the reaction efficiency was better when the pH was about 7.0.

ZV0512 was taken as an example in the C-Lock method.

A. Coupling:

The drug to be coupled (Duostatin 5) (Compound 27 in Example 1) was dissolved in 60% acetonitrile/water to prepare a 10 mM stock solution.

0.5 molar equivalents of drug were added into a solution of the reduced 5T4 antibody every 5 minutes until the final drug concentration was 4.5 eq. The reaction was mixed on a rotator at room temperature.

The reaction was carried out via HIC-HPLC to analyze the conjugation curve. Unbound antibody should be 0%, DAR 4 peak should be ≥70%.

B. Purification

If the ADC product was a heterogeneous mixture containing ADCs of DAR 2-4, the free drug was removed by buffer exchange using an Amicon rotary concentrator. The buffer was 50 mM sodium phosphate+30% propylene glycol.

If a homogeneous DAR 3 peak was desired, the product was purified on a hydrophobic column to remove ADCs with unwanted DAR.

The antibody-drug conjugates were loaded onto a hydrophobic chromatography column (HIC) and purified, thereby obtaining anti-5T4 ADCs with a coupling number of 4.

The structures of antibody-drug conjugates prepared in the examples are shown in the following table.

TABLE 1

Antibody-drug conjugate structure

| No. | Drug | Linker (L) | Coupling method | DAR |
|---|---|---|---|---|
| ZV0501 | MMAF | MC | SeaGen method | 3.5-4.0 |
| ZV0508 | Duostatin 5 | VC | C-Lock | 4 |
| ZV0503 | Duostatin 3 | cHex | C-Lock | 4 |
| ZV0504 | Duostatin 14 | AAN | C-Lock | 4 |
| ZV0505 | Duostatin 14 | VC | C-Lock | 4 |
| ZV0519 | Duomycin 2 | Disulfide bond | C-Lock | 4 |
| ZV0515 | Duomycin 4 | VA | C-Lock | 4 |
| ZV0516 | Duomycin 4 | AAN | C-Lock | 4 |
| ZV0512 | Calicheamicin | Asn-Ala | K-Lock | 2 |
| ZV0513 | Calicheamicin | Asn-Ala | C-Lock | 4 |
| ZV0517 | Amanitine | VC-PAB | K-Lock | 2 |
| ZV0518 | Amanitine | AAN-PAB | C-Lock | 4 |

One representative ADC was taken for HIC analysis. The steps are as follows:

TSKgel Butyl-NPR column (4.6 mm ID×3.5 cm, 2.5 mm, Tosoh Bioscience, Montgomeryville, Pa.) was used and mobile phases were 1.5M ammonium sulfate+0.025M sodium phosphate buffer (pH 7) and 75% 0.025M sodium phosphate buffer+25% isopropanol (pH 7.0). Gradient elution: 10% B to 70% B, 10 min; 70% B to 100% B, 5 min; 100% B to 10% B, 2 min.

FIG. 1 shows the results of HIC analysis of the ADC ZV0508 according to the present invention.

Example 4 Affinity Test

The experimental steps for testing affinity were as follows:

ZV05 and ZV0508 were diluted to a concentration of 10 μg/ml, and further diluted by a 3-fold gradient to a final concentration of 10, 3.3, 1.1, and 0.33 μg/ml, respectively, and added into an EP tube containing $3.0 \times 10^5$ MDA-MB-468 cells, respectively, and incubated at 4° C. for 30 min.

Figure 2:
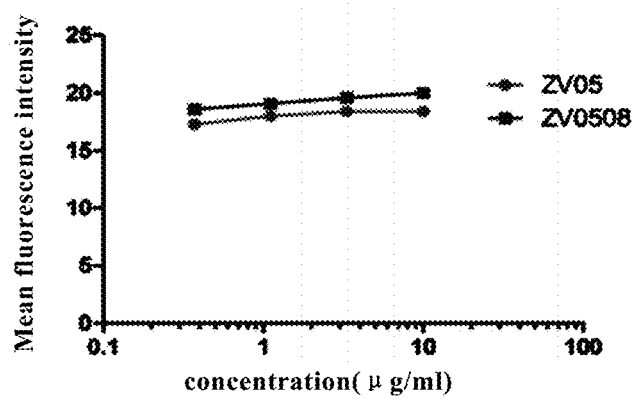
FIG. 2 shows that the affinity of ADC ZV0508 is not effected.

The cells were pelleted by centrifugation and washed once with PBS. Then 600 μl of FITC-labeled secondary antibody dilution was added and incubated for 30 min at 4° C. in darkness. The cells were pelleted by centrifugation, washed twice with PBS, and finally, the cells were suspended by adding 500 μl of PBS. The average fluorescence intensity value was measured by flow cytometry. The test results were as follows:

The affinity of anti-5T4 antibody of the present invention before and after coupling was compared. The affinity test result of the representative ADC ZV0508 was shown in FIG. 2. It can be seen from the figure that antibody affinity before and after coupling is not changed.

Example 5 Detection of Endocytosis

Figure 3:
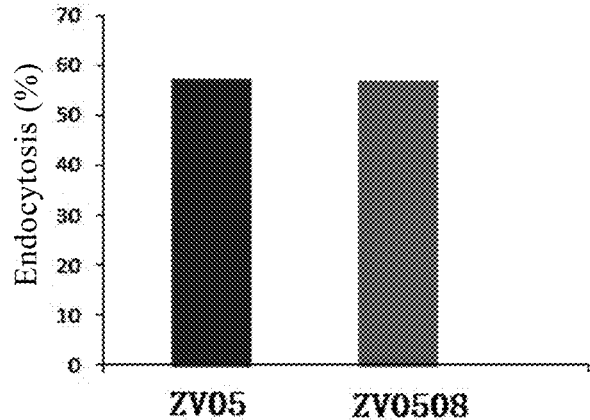
FIG. 3 shows antibody ZV05 and ADC ZV0508 have strong endocytosis on cells.

The experimental steps of endocytosis experiment were as follows:

ZV05 and ZV0508 were diluted to a concentration of 10 μg/ml, and added into an EP tube containing 3.0×10⁵ MDA-M13-468 cells, respectively, and incubated at 4° C. for 30 min. The cells were pelleted by centrifugation and washed once with PBS. The cells in each EP tube were divided into two aliquots, wherein one was incubated at 4° C. for 2 h, and the other was incubated at 37° C. for 2 h. The cells were pelleted by centrifugation and washed once with PBS. Then 600 μl of FITC-labeled secondary antibody dilution was added into each EP tube and incubated for 30 min at 4 in darkness. The cells were pelleted by centrifugation, washed twice with PBS, and finally suspended in 500 μl of PBS. The mean fluorescence intensity value was measured by flow cytometry. Endocytosis was calculated by using the following formula: Endocytosis rate (%)=(MFI$_{4° C.}$-MFI$_{37° C.}$)/MFI$_{4° C.}$. The test results were as follows:

The results of the endocytosis of the representative ADC ZV0508 are shown in FIG. 3. It can be seen from the figure that the antibody (ZV05) and the ADC (ZV0508) have strong endocytosis on the cells.

Example 6 Cell Cycle Inhibition Experiment of Tumor Cells

In this example, the inhibitory activity of the ADCs of the present invention on 5T4-positive cells was examined. The tumor cell lines in this example were all purchased from ATCC, USA.

The experimental steps were as follows:

MDA-MB-468 cells were seeded into 6-well plates at 5.0×10⁴ cells/well, and cultured in a 37° C. cell culture incubator. After the cells were attached, ZV05 and ZV0508 were diluted to 5 μg/ml and added to 6-well plates. After culturing was continued for 48 h to 72 h, the cell cycle detection kit of Biyuntian was used to measure the DNA content by flow cytometry according to the procedure of the instructions, and the cell cycle was analyzed.

Figure 4:
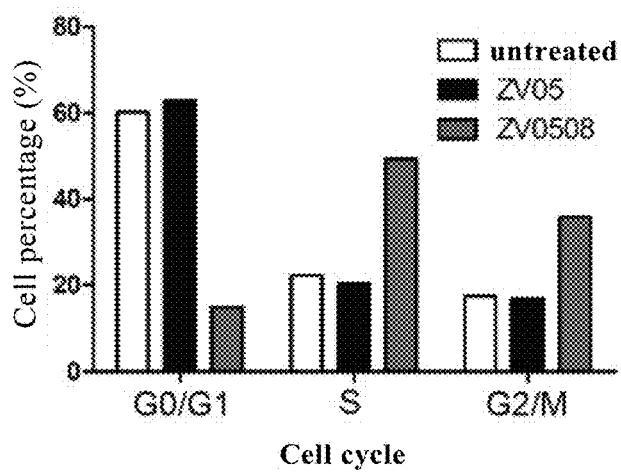
FIG. 4 shows ADC ZV0508 represses the cell cycle in G2/M phase.

The experimental results showed that, under the action of medicine, the ADC ZV0508 stopped the cell cycle in G2/M phase, and the results were shown in FIG. 4. In FIG. 4, ZV05 is an antibody control without conjugating drug.

Example 7 In Vivo Antitumor Activity

The steps for in vivo anti-tumor activity detection of anti-5T4 ADCs were as follows:

Tumor cells were inoculated into the sputum of nude mice or Scid mice. When the tumor volume was 100-300 mm³, medicines were given through tail vein. 0E19 was administered three times, once every three days. Other models were single administration, and tumor sizes were timing-measured after administration. The long diameter (a) and short diameter (b) of a tumor mass were measured, and the tumor volume (TV) was calculated as: TV=1/2×a×b².

The experimental results showed that the anti-5T4 ADCs of the present invention had a significant inhibitory effect on tumors in vivo, and the tumor inhibitory activity in vivo was higher than that of the control antibody (humanized A1 antibody).

Figure 5:
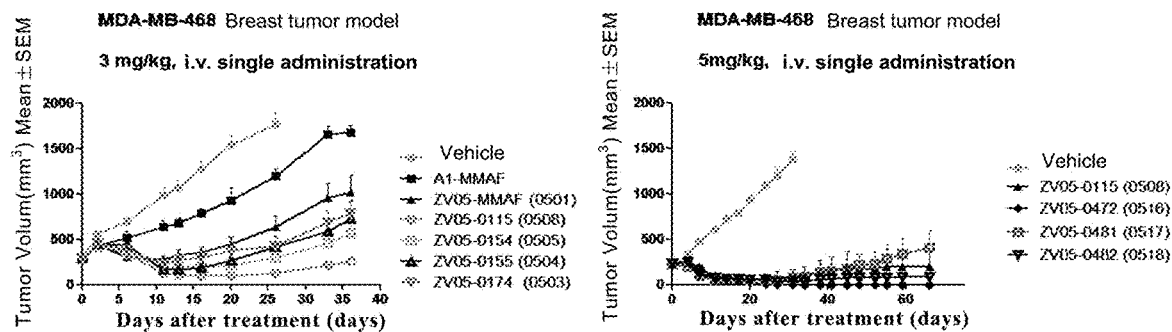
FIG. 5 shows the efficacy (+++) of ADC in the treatment of MDA-MB-468 breast cancer xenograft in mice.

FIG. 5 shows the efficacy (+++) of ADC in the treatment of MDA-MB-468 breast cancer xenograft in mice.

Figure 6:
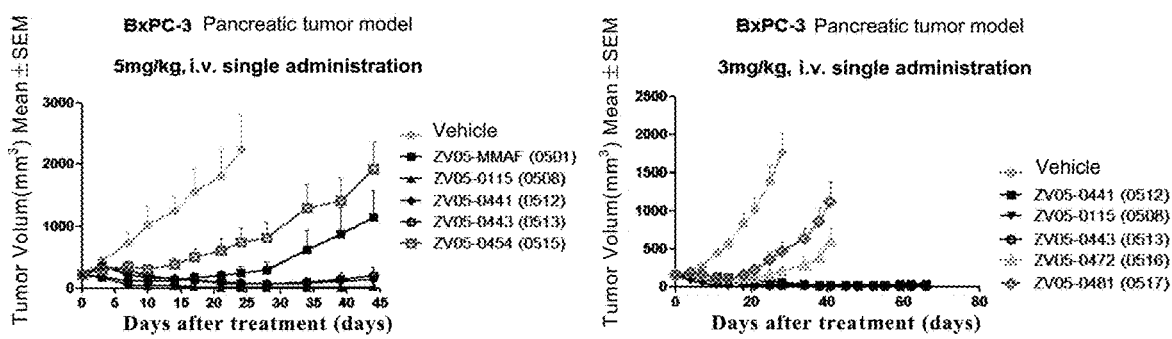
FIG. 6 shows the efficacy (++) of ADC in the treatment of BxPC-3 pancreatic cancer xenograft in mice.

FIG. 6 shows the efficacy (++) of ADC in the treatment of BxPC-3 pancreatic cancer xenograft in mice.

Figure 7:
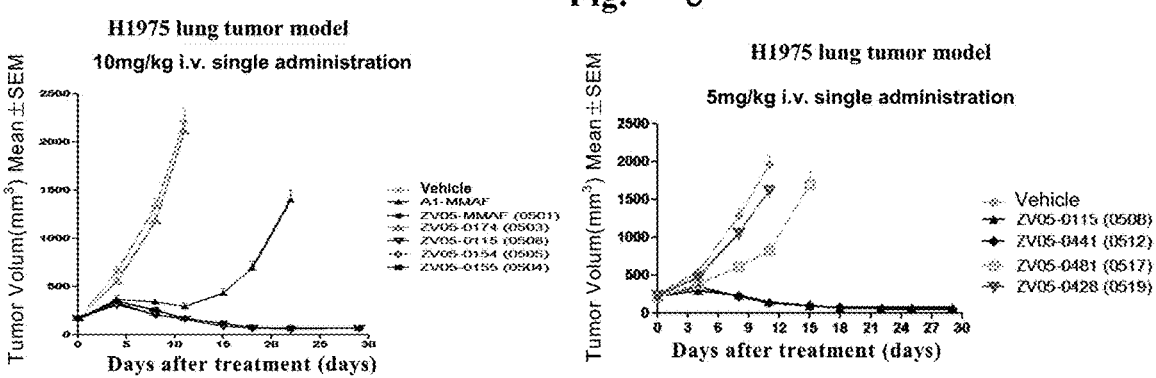
FIG. 7 shows the efficacy (+++) of ADC in the treatment of H1975 lung cancer xenograft in mice.

FIG. 7 shows the efficacy (+++) of ADC in the treatment of H1975 lung cancer xenograft in mice.

Figure 8:
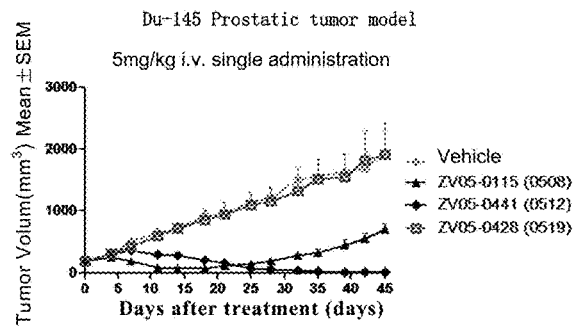
FIG. 8 shows the efficacy (+++) of ADC in the treatment of DU-145 prostate cancer xenograft in mice.

FIG. 8 shows the efficacy (+++) of ADC in the treatment of DU-145 prostate cancer xenograft in mice.

Figure 9:
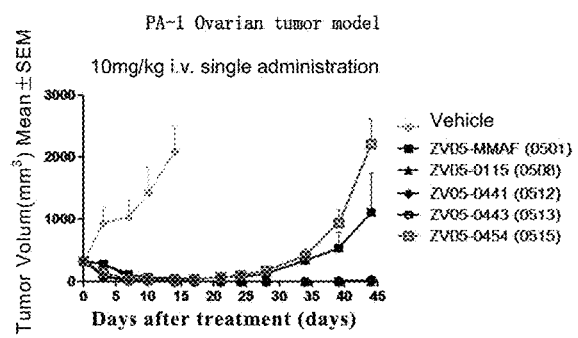
FIG. 9 shows the inhibitory effect (+) of the ADC of PA-1 ovarian cancer xenograft in mice.

FIG. 9 shows the efficacy (+) of ADC in the treatment of PA-1 ovarian cancer xenograft in mice.

Figure 10:
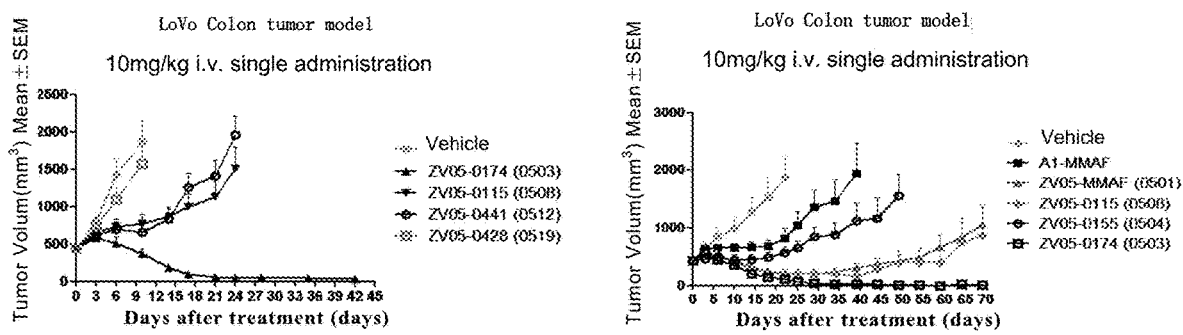
FIG. 10 shows the inhibitory effect (+) of the ADC of Lovo colon cancer xenograft in mice.

FIG. 10 shows the efficacy (+) of ADC in the treatment of Lovo colon cancer xenograft in mice.

The tumor inhibitory effect of the control ADC (A1-MMAF) was significantly lower than that of the ADC of the present invention.

In the figures, the tested ADCs include:
ZV05-MMAF(0501), ie ZV0501;
ZV05-0115(0508), ie ZV0508;
ZV05-0154(0505), ie ZV0505;
ZV05-0155(0504), ie ZV0504;
ZV05-0174(0503), ie ZV0503;
ZV05-0472(0516), ie ZV0516;
ZV05-0481(0517), ie ZV0517;
ZV05-0482(0518), ie ZV0518;
ZV05-0441(0512), ie ZV0512;
ZV05-0443(0513), ie ZV0513;
ZV05-0454(0515), ie ZV0515;
ZV05-0428(0519), ie ZV0519.

A1-MMAF is an ADC produced by ligation of the tubulin inhibitor MMAF to a humanized anti-5T4 monoclonal antibody A1 by conventional antibody disulfide bond reduction, prepared by the method described in US2012251558, wherein DAR is approximately 4.

The test results (FIGS. 5-10) show that the ADCs of the present invention (including ZV0508, ZV0512, ZV0513, ZV0503, etc.) have a significantly better tumor inhibitory effect than that of the control ADC (A1-MMAF). ZV0508, ZV0512, ZV0513 and ZV0503 have the most superior inhibitory effect.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be in the scope of the invention defined by the appended claims of the application.

The invention claimed is:

1. An antibody-drug conjugate or a pharmaceutically acceptable salt thereof, wherein the antibody-drug conjugate comprises an antibody and a drug coupled with the antibody, and the antibody comprises a heavy chain variable region and a light chain variable region, wherein, the heavy chain variable region comprises three complementary determining regions:

CDR1:
(SEQ ID NO.: 1)
GFTFSSYE

CDR2:
(SEQ ID NO.: 2)
ISSSGSTI
and

CDR3:
(SEQ ID NO.: 3)
AREMQFGWELLGAFDI;

wherein, the light chain variable region comprises three complementary determining regions:

CDR1':
(SEQ ID NO.: 4)
QSVSSSY

CDR2':
(SEQ ID NO.: 5)
GAS
and

CDR3':
(SEQ ID NO.: 6)
QQYGSS;

and the heavy chain variable region has an amino acid sequence as shown in SEQ ID NO: 7.

2. The antibody-drug conjugate or a pharmaceutically acceptable salt thereof according to claim 1, wherein the light chain variable region has an amino acid sequence as shown in SEQ ID NO: 8.

3. The antibody-drug conjugate or a pharmaceutically acceptable salt thereof according to claim 1, wherein the antibody comprises the heavy chain as shown in SEQ ID NO: 9.

4. The antibody-drug conjugate or a pharmaceutically acceptable salt thereof according to claim 1, wherein the antibody comprises the light chain as shown in SEQ ID NO: 10.

5. The antibody-drug conjugate or a pharmaceutically acceptable salt thereof according to claim 1, wherein the light chain constant region of the antibody-drug conjugate is coupled with at least one drug molecule, and the drug molecule is linked to a lysine site of the light chain constant region.

6. The antibody-drug conjugate or a pharmaceutically acceptable salt thereof according to claim 1, wherein the drug is a small molecule drug selected from the group consisting of: Duostatin 5, MMAF, Duostatin 14, Duomycin 2, Duomycin 4, Calicheamicin, and Amanitine.

7. The antibody-drug conjugate or a pharmaceutically acceptable salt thereof according to claim 1, wherein the structure of the antibody-drug conjugate is as shown in Formula I:

Ab-(L-D)n      I wherein:
Ab is an antibody;
L is absent or a linker connecting the antibody and the drug;
D is a small molecule drug that inhibits tumor cells;
n is the average number of drugs coupled to the antibody; and
"-" is a bond or a linker.

8. The antibody-drug conjugate or a pharmaceutically acceptable salt thereof according to claim 7, wherein n is from 1 to 4.

9. The antibody-drug conjugate or a pharmaceutically acceptable salt thereof according to claim 7, wherein n is from 1.5 to 3.5.

10. The antibody-drug conjugate or a pharmaceutically acceptable salt thereof according to claim 7, wherein n is from 1.8 to 2.

11. The antibody-drug conjugate or a pharmaceutically acceptable salt thereof according to claim 7, wherein the drug molecule is a small molecule drug that inhibits tumor cells.

12. The antibody-drug conjugate or a pharmaceutically acceptable salt thereof according to claim 7, wherein D is selected from the group consisting of: Duostatin 5, MMAF, Duostatin 14, Duomycin 2, Duomycin 4, Calicheamicin, and Amanitine.

13. The antibody-drug conjugate or a pharmaceutically acceptable salt thereof according to claim 7, wherein the structure of the antibody-drug conjugate is as shown in Formula III:

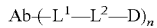

in Formula III, the structure of $L^1$—$L^2$ is selected from L-1, L-2 or L-3:

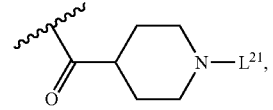

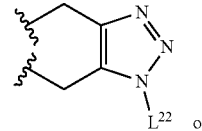

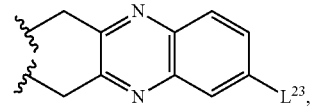

wherein each of $L^{21}$, $L^{22}$, $L^{23}$ is independently a linker selected from the group consisting of —(CH2)n-, —(CH2CH2O)n-, Val-Cit, Ala-Ala-Asn, and a combination thereof;
Ab, D, and n as defined in claim 7;
the wavy line indicates the connection position with antibody.

14. The antibody-drug conjugate or a pharmaceutically acceptable salt thereof according to claim 1, wherein the antibody-drug conjugate is selected from the group consisting of: ZV0508, ZV0512, ZV0513, ZV0501, ZV0503, ZV0504, ZV0517, ZV0518, ZV0505, ZV0516, ZV0515, and ZV0519;
wherein the structure of conjugate ZV0508 is shown as follows:

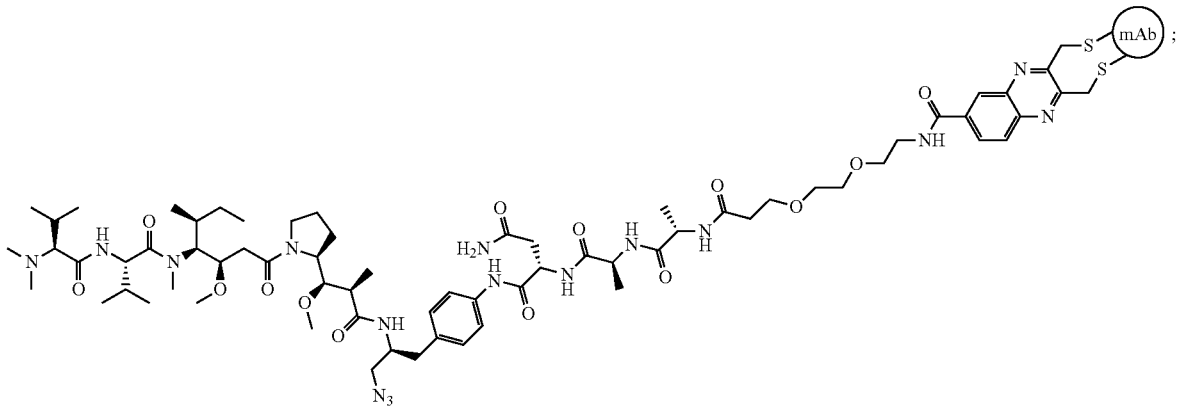

the structure of conjugate ZV0512 is shown as follows:
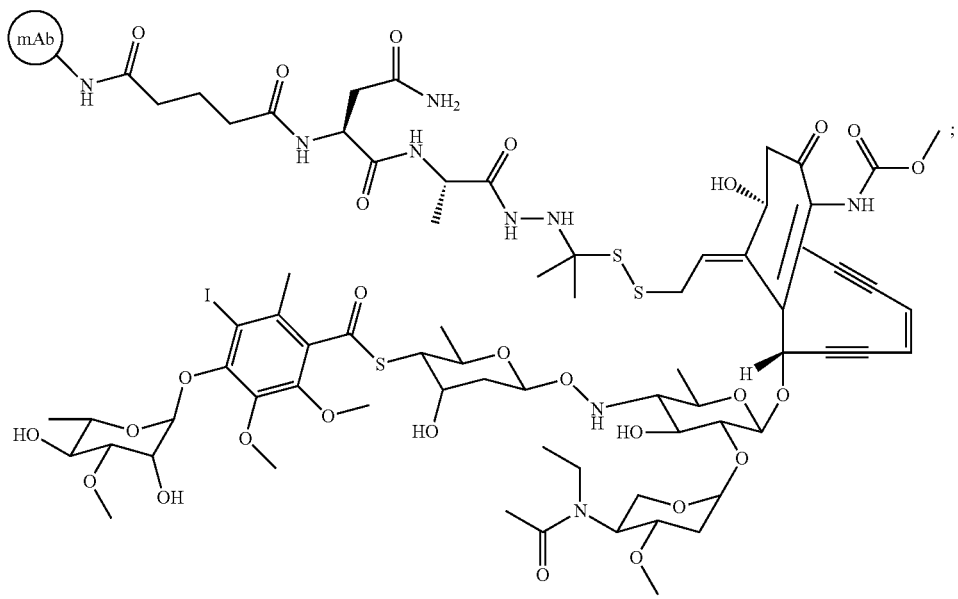
the structure of conjugate ZV0513 is shown as follows:
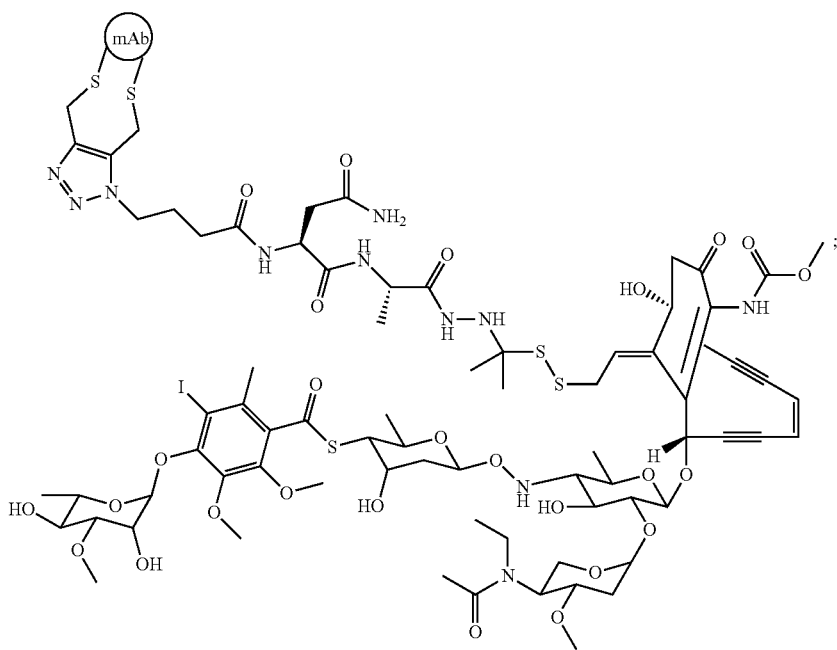

the structure of conjugate ZV0501 is shown as follows:
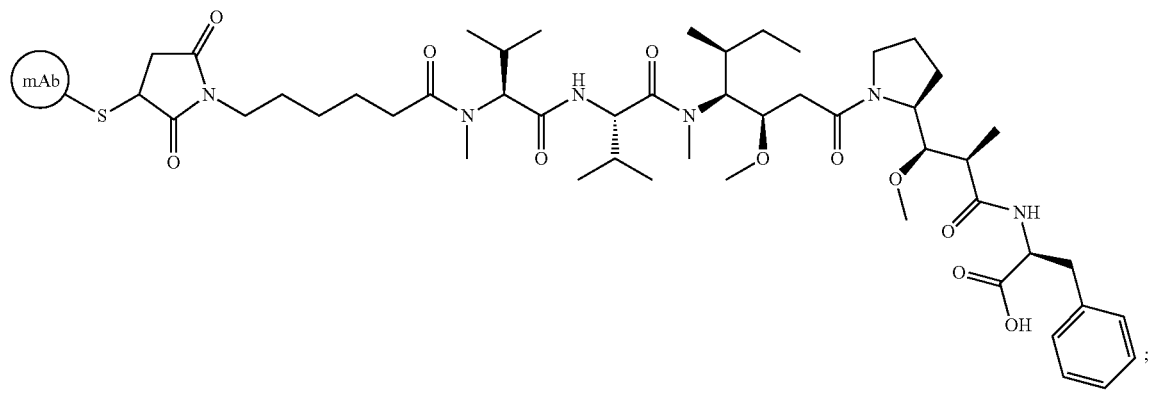 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)CC(SC)C1=O)C(C)C]
the structure of conjugate ZV0503 is shown as follows:
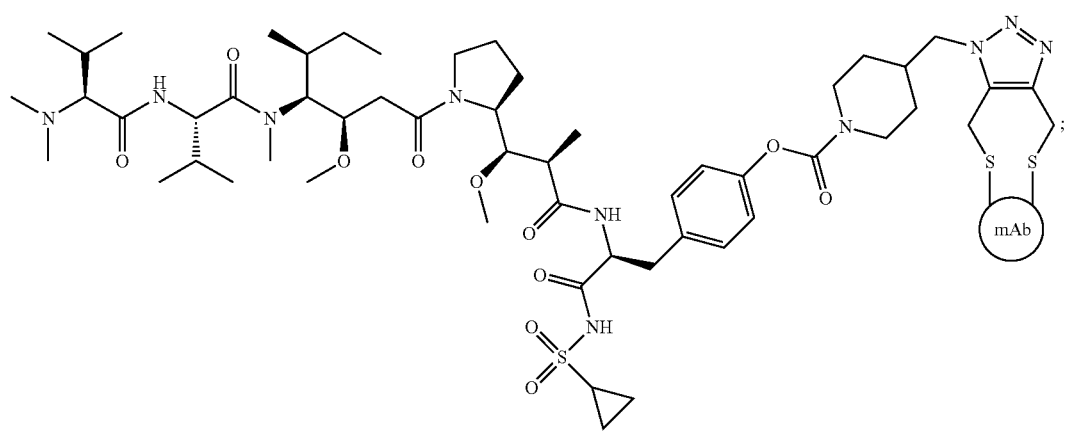 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(Cn3nnc(CSC)c3CSC)CC2)cc1)C(=O)NS(=O)(=O)C1CC1)OC)N(C)C(=O)[C@@H](NC(=O)[C@H](C(C)C)N(C)C)C(C)C]
the structure of conjugate ZV0504 is shown as follows:
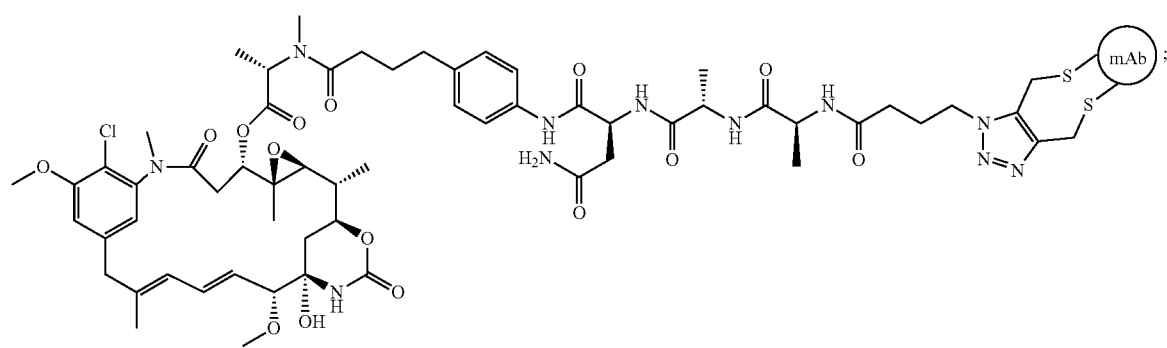

the structure of conjugate ZV0517 is shown as follows:
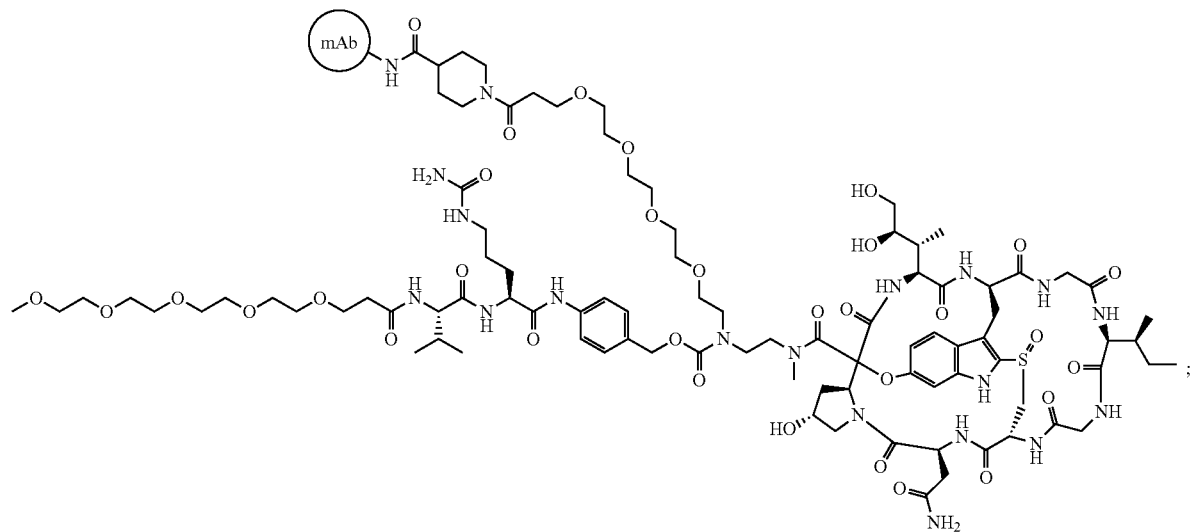 [SMILES: CC[C@H](C)[C@@H]1NC(=O)CNC(=O)[C@H]2Cc3c4[nH]c5cc(ccc35)OC(C(=O)N(C)CCN(CCOCCOCCOCCOCCC(=O)N3CCC(C(=O)NC)CC3)C(=O)OCc3ccc(NC(=O)[C@H](CCCNC(N)=O)NC(=O)[C@@H](NC(=O)CCOCCOCCOCCOCCOC)C(C)C)cc3)(C(=O)N[C@@H]([C@@H](C)[C@@H](O)CO)C(=O)N2)[C@@H]2C[C@@H](O)CN2C(=O)[C@H](CC(N)=O)NC(=O)[C@H](CS4=O)NC(=O)CNC1=O]
the structure of conjugate ZV0518 is shown as follows:
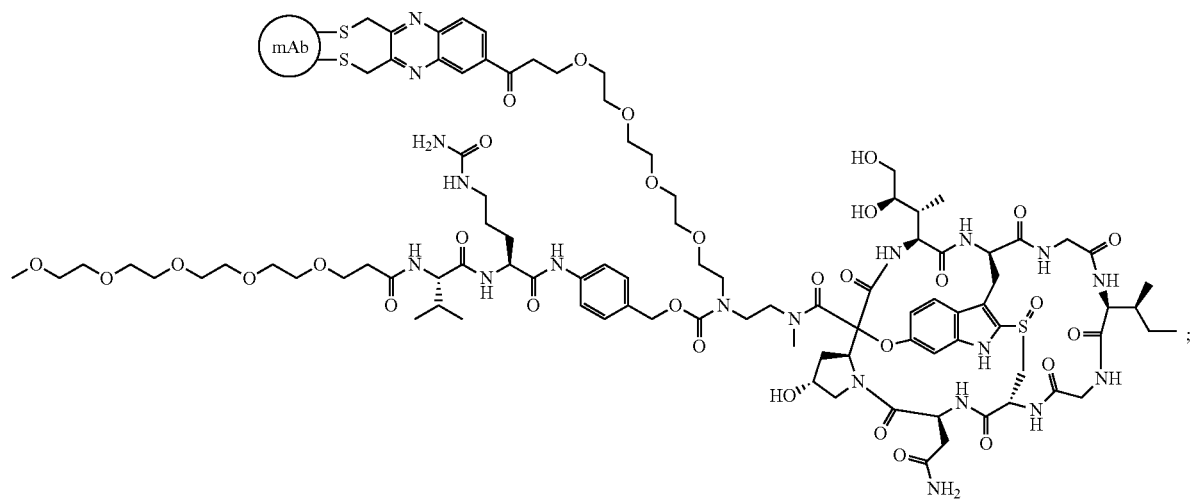 [SMILES: CC[C@H](C)[C@@H]1NC(=O)CNC(=O)[C@H]2Cc3c4[nH]c5cc(ccc35)OC(C(=O)N(C)CCN(CCOCCOCCOCCOCCC(=O)c3ccc5nc(CSC)c(CSC)nc5c3)C(=O)OCc3ccc(NC(=O)[C@H](CCCNC(N)=O)NC(=O)[C@@H](NC(=O)CCOCCOCCOCCOCCOC)C(C)C)cc3)(C(=O)N[C@@H]([C@@H](C)[C@@H](O)CO)C(=O)N2)[C@@H]2C[C@@H](O)CN2C(=O)[C@H](CC(N)=O)NC(=O)[C@H](CS4=O)NC(=O)CNC1=O]
the structure of conjugate ZV0505 is shown as follows:
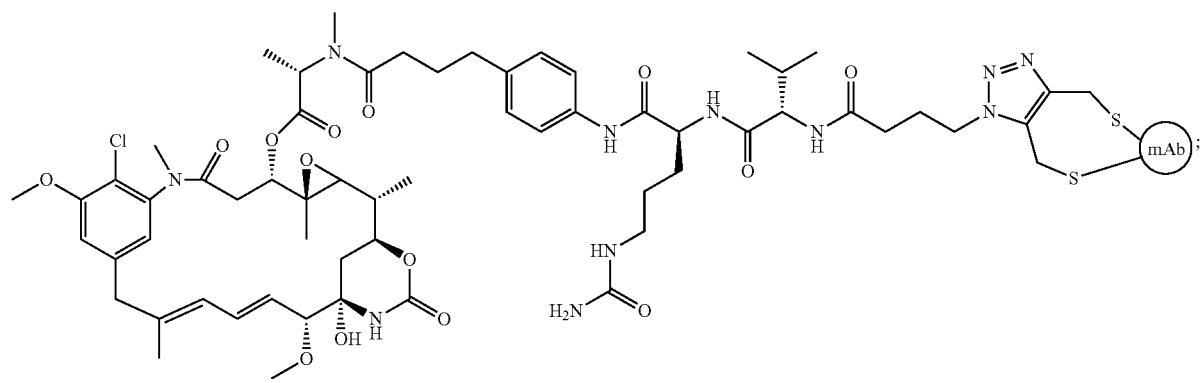

the structure of conjugate ZV0516 is shown as follows:
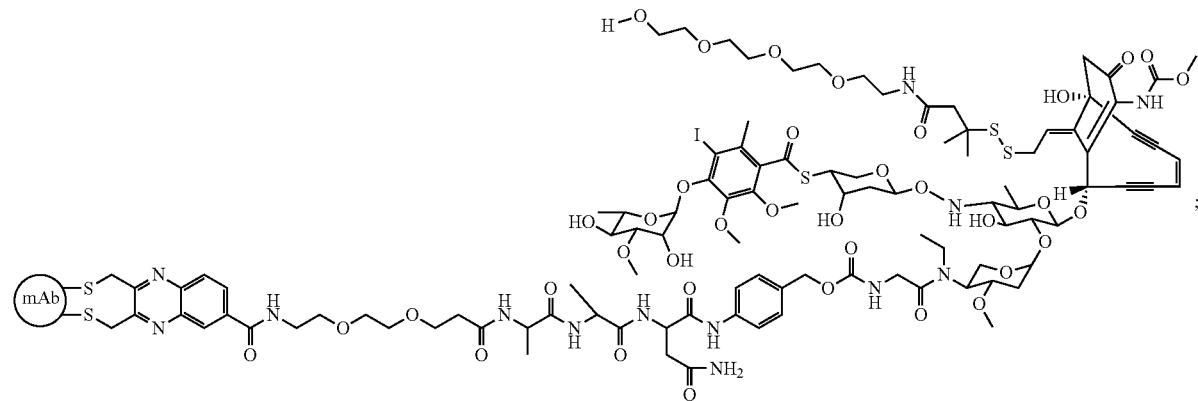
the structure of conjugate ZV0515 is shown as follows:
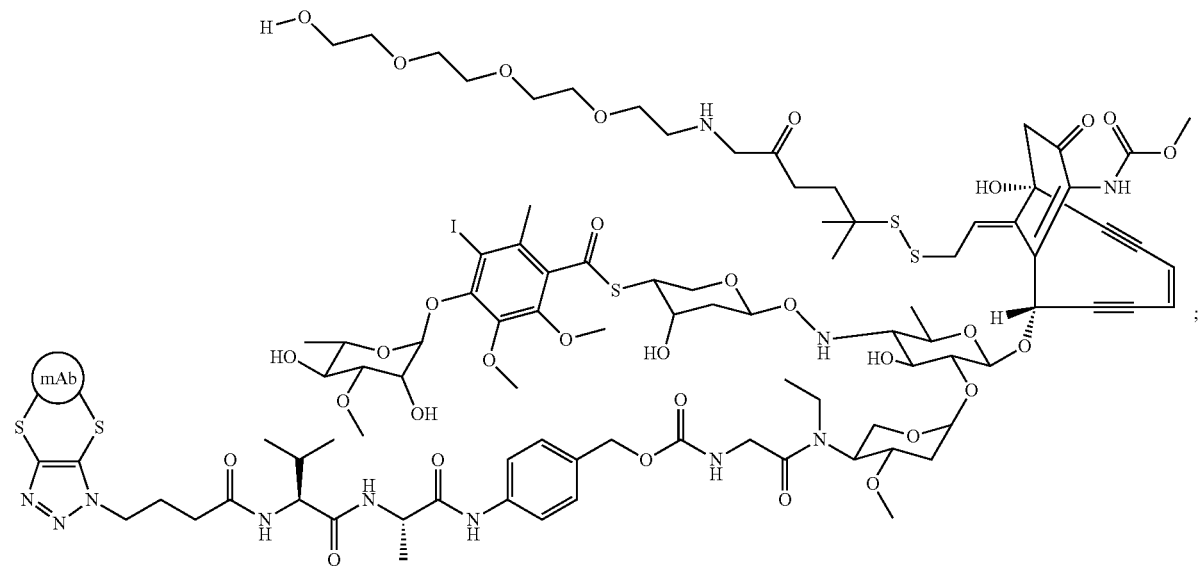

the structure of conjugate ZV0519 is shown as follows:
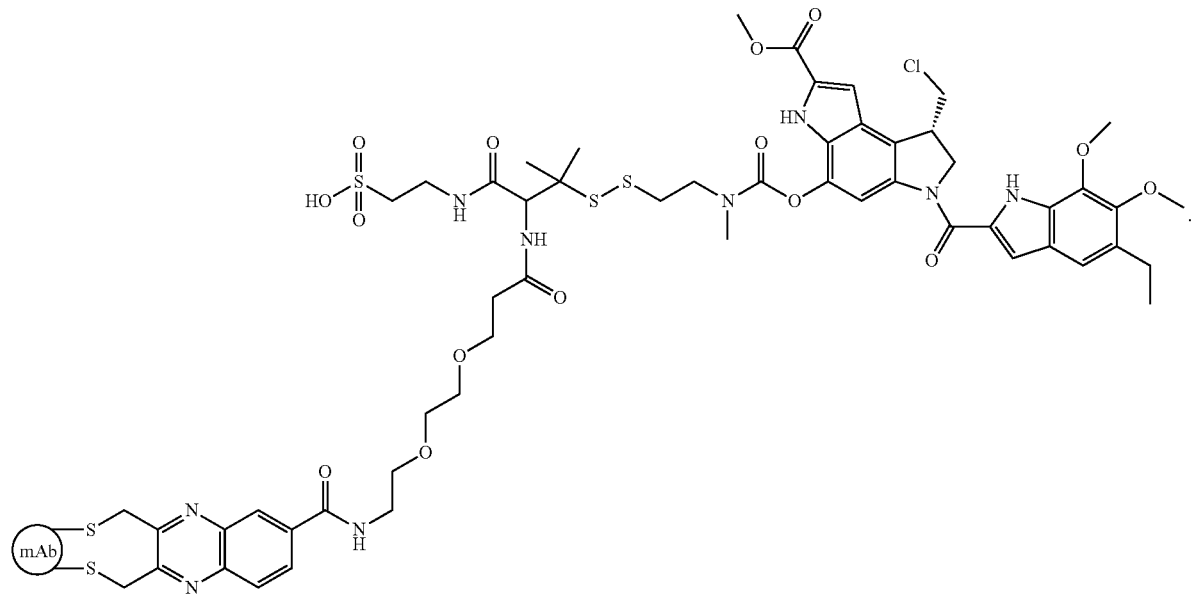
15. The antibody-drug conjugate or a pharmaceutically acceptable salt thereof according to claim 1, wherein the antibody-drug conjugate is selected from the group consisting of: ZV0508, ZV0512, ZV0513, and ZV0503,
wherein the structure of conjugate ZV0508 is shown as follows:
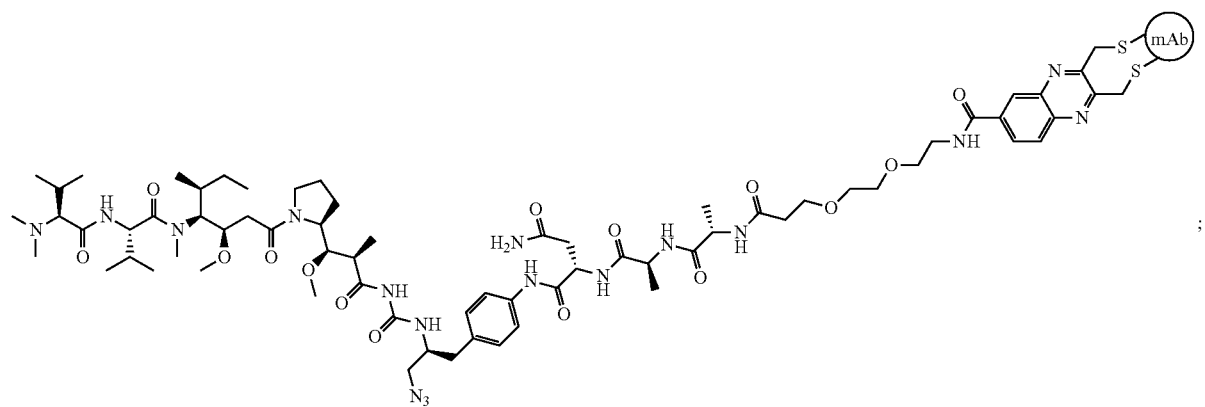

the structure of conjugate ZV0512 is shown as follows:
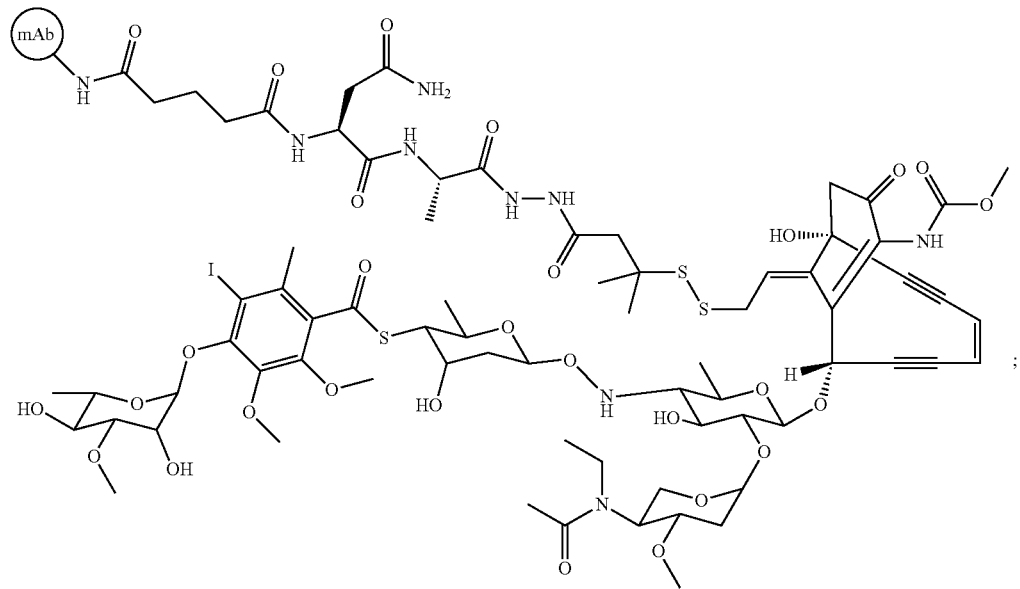
the structure of conjugate ZV0513 is shown as follows:
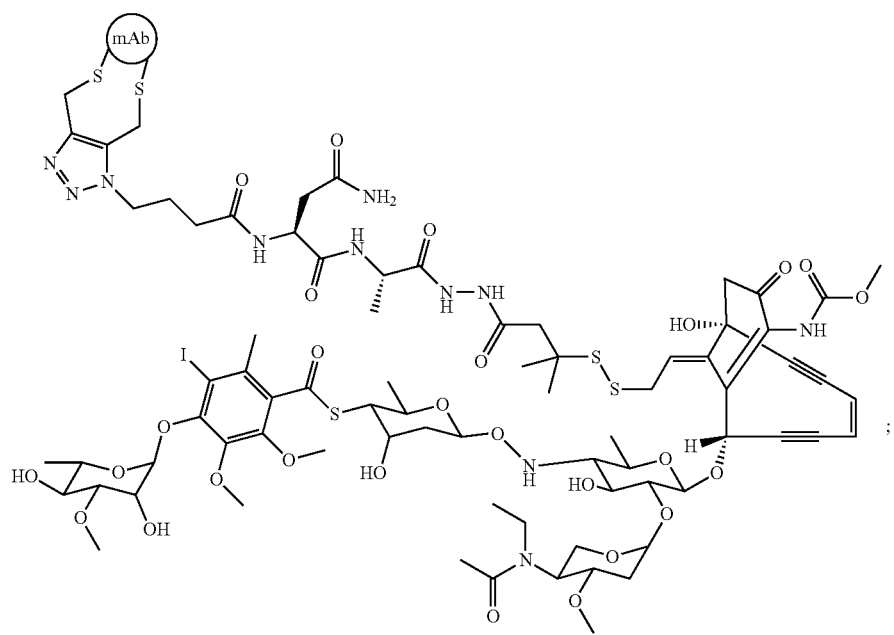

the structure of conjugate ZV0503 is shown as follows:

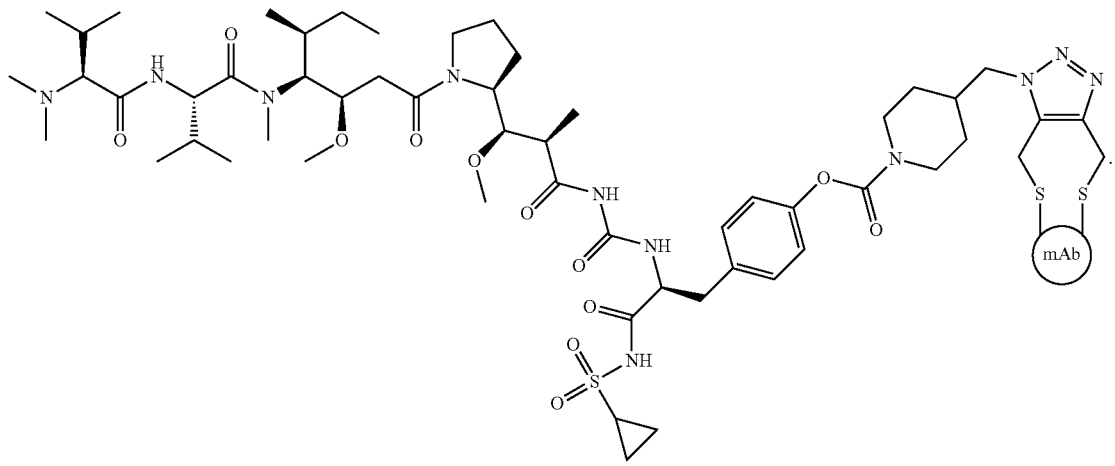

16. A pharmaceutical composition which comprises an antibody-drug conjugate according to claim 1, and a pharmaceutically acceptable carrier.

17. A method for preparing the antibody-drug conjugate of claim 1, which comprises the following steps:
configuring a reaction system which comprises an antibody and a free drug molecule, and then performing a coupling reaction to prepare the antibody-drug conjugate,
wherein the drug molecule includes a linker.

18. A method of treating a tumor, which comprises a step of administering the antibody-drug conjugate of claim 1 to a subject in need thereof.

19. The method of claim 18, wherein the tumor is 5T4 positive tumor.

20. The method of claim 18, wherein the tumor is selected from the group consisting of breast cancer, gastric cancer, ovarian cancer, and lung cancer.

* * * * *

SEQUENCE LISTING

<160> NUMBER OF SEQ ID NOS: 12

<210> SEQ ID NO 1
<211> LENGTH: 8
<212> TYPE: PRT

```
<213> ORGANISM: Artificial sequence
<220> FEATURE:
<223> OTHER INFORMATION: Synthetic

<400> SEQUENCE: 1

Gly Phe Thr Phe Ser Ser Tyr Glu
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic

<400> SEQUENCE: 2

Ile Ser Ser Ser Gly Ser Thr Ile
1               5

<210> SEQ ID NO 3
<211> LENGTH: 16
<212> TYPE: PRT
<213> ORGANISM: Artificial sequence
<220> FEATURE:
<223> OTHER INFORMATION: Synthetic

<400> SEQUENCE: 3

Ala Arg Glu Met Gln Phe Gly Trp Glu Leu Leu Gly Ala Phe Asp Ile
1               5                   10                  15

<210> SEQ ID NO 4
<211> LENGTH: 7
<212> TYPE: PRT
<213> ORGANISM: Artificial sequence
<220> FEATURE:
<223> OTHER INFORMATION: Synthetic

<400> SEQUENCE: 4

Gln Ser Val Ser Ser Ser Tyr
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic

<400> SEQUENCE: 5

Gly Ala Ser
1

<210> SEQ ID NO 6
<211> LENGTH: 6
<212> TYPE: PRT
<213> ORGANISM: Artificial sequence
<220> FEATURE:
<223> OTHER INFORMATION: Synthetic

<400> SEQUENCE: 6

Gln Gln Tyr Gly Ser Ser
1               5

<210> SEQ ID NO 7
<211> LENGTH: 142
<212> TYPE: PRT
<213> ORGANISM: Artificial sequence
```

<220> FEATURE:
<223> OTHER INFORMATION: Synthetic

<400> SEQUENCE: 7

Met Asp Trp Thr Trp Arg Phe Leu Phe Val Val Ala Ala Ala Thr Gly
1               5                   10                  15

Val Gln Ser Gln Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Glu Met Asn Trp Val Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Met Gln Phe Gly Trp Glu Leu Leu Gly Ala
        115                 120                 125

Phe Asp Ile Trp Gly Gln Gly Thr Met Val Thr Val Ser Ser
    130                 135                 140

<210> SEQ ID NO 8
<211> LENGTH: 127
<212> TYPE: PRT
<213> ORGANISM: Artificial sequence
<220> FEATURE:
<223> OTHER INFORMATION: Synthetic

<400> SEQUENCE: 8

Met Asp Met Arg Val Pro Ala Gln Leu Leu Gly Leu Leu Leu Leu Trp
1               5                   10                  15

Leu Ser Gly Ala Arg Cys Glu Ile Val Leu Thr Gln Ser Pro Gly Thr
            20                  25                  30

Leu Ser Leu Ser Pro Gly Glu Arg Ala Thr Leu Ser Cys Arg Ala Ser
        35                  40                  45

Gln Ser Val Ser Ser Ser Tyr Leu Ala Trp Tyr Gln Gln Lys Pro Gly
    50                  55                  60

Gln Ala Pro Arg Leu Leu Ile Tyr Gly Ala Ser Ser Arg Ala Thr Gly
65                  70                  75                  80

Ile Pro Asp Arg Phe Ser Gly Ser Gly Ser Gly Thr Asp Phe Thr Leu
                85                  90                  95

Thr Ile Ser Arg Leu Glu Pro Glu Asp Phe Ala Val Tyr Tyr Cys Gln
            100                 105                 110

Gln Tyr Gly Ser Ser Phe Gly Gln Gly Thr Lys Leu Glu Ile Lys
        115                 120                 125

<210> SEQ ID NO 9
<211> LENGTH: 472
<212> TYPE: PRT
<213> ORGANISM: Artificial sequence
<220> FEATURE:
<223> OTHER INFORMATION: Synthetic

<400> SEQUENCE: 9

Met Asp Trp Thr Trp Arg Phe Leu Phe Val Val Ala Ala Ala Thr Gly
1               5                   10                  15

```
Val Gln Ser Gln Val Gln Leu Val Gln Ser Gly Gly Gly Leu Val Gln
             20                  25                  30

Pro Gly Gly Ser Leu Arg Leu Ser Cys Ala Ala Ser Gly Phe Thr Phe
             35                  40                  45

Ser Ser Tyr Glu Met Asn Trp Val Arg Gln Ala Pro Gly Lys Gly Leu
             50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
             100                 105                 110

Tyr Tyr Cys Ala Arg Glu Met Gln Phe Gly Trp Glu Leu Leu Gly Ala
             115                 120                 125

Phe Asp Ile Trp Gly Gln Gly Thr Met Val Thr Val Ser Ser Ala Ser
             130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                 165                 170                 175

Glu Pro Val Thr Val Ser Trp Asn Ser Gly Ala Leu Thr Ser Gly Val
             180                 185                 190

His Thr Phe Pro Ala Val Leu Gln Ser Ser Gly Leu Tyr Ser Leu Ser
             195                 200                 205

Ser Val Val Thr Val Pro Ser Ser Ser Leu Gly Thr Gln Thr Tyr Ile
             210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                 245                 250                 255

Pro Glu Leu Leu Gly Gly Pro Ser Val Phe Leu Phe Pro Pro Lys Pro
             260                 265                 270

Lys Asp Thr Leu Met Ile Ser Arg Thr Pro Glu Val Thr Cys Val Val
             275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                 325                 330                 335

Asp Trp Leu Asn Gly Lys Glu Tyr Lys Cys Lys Val Ser Asn Lys Ala
             340                 345                 350

Leu Pro Ala Pro Ile Glu Lys Thr Ile Ser Lys Ala Lys Gly Gln Pro
             355                 360                 365

Arg Glu Pro Gln Val Tyr Thr Leu Pro Pro Ser Arg Asp Glu Leu Thr
             370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                 405                 410                 415

Lys Thr Thr Pro Pro Val Leu Asp Ser Asp Gly Ser Phe Phe Leu Tyr
             420                 425                 430

Ser Lys Leu Thr Val Asp Lys Ser Arg Trp Gln Gln Gly Asn Val Phe
```

```
                    435                 440                 445
Ser Cys Ser Val Met His Glu Ala Leu His Asn His Tyr Thr Gln Lys
    450                 455                 460
Ser Leu Ser Leu Ser Pro Gly Lys
465                 470

<210> SEQ ID NO 10
<211> LENGTH: 234
<212> TYPE: PRT
<213> ORGANISM: Artificial sequence
<220> FEATURE:
<223> OTHER INFORMATION: Synthetic

<400> SEQUENCE: 10

Met Asp Met Arg Val Pro Ala Gln Leu Leu Gly Leu Leu Leu Leu Trp
1               5                   10                  15
Leu Ser Gly Ala Arg Cys Glu Ile Val Leu Thr Gln Ser Pro Gly Thr
                20                  25                  30
Leu Ser Leu Ser Pro Gly Glu Arg Ala Thr Leu Ser Cys Arg Ala Ser
            35                  40                  45
Gln Ser Val Ser Ser Tyr Leu Ala Trp Tyr Gln Gln Lys Pro Gly
50                  55                  60
Gln Ala Pro Arg Leu Leu Ile Tyr Gly Ala Ser Ser Arg Ala Thr Gly
65                  70                  75                  80
Ile Pro Asp Arg Phe Ser Gly Ser Gly Ser Gly Thr Asp Phe Thr Leu
                85                  90                  95
Thr Ile Ser Arg Leu Glu Pro Glu Asp Phe Ala Val Tyr Tyr Cys Gln
                100                 105                 110
Gln Tyr Gly Ser Ser Phe Gly Gln Gly Thr Lys Leu Glu Ile Lys Arg
            115                 120                 125
Thr Val Ala Ala Pro Ser Val Phe Ile Phe Pro Pro Ser Asp Glu Gln
130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 11
<211> LENGTH: 449
<212> TYPE: PRT
<213> ORGANISM: Artificial sequence
<220> FEATURE:
<223> OTHER INFORMATION: Synthetic

<400> SEQUENCE: 11

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Phe
                20                  25                  30
```

```
Gly Met Asn Trp Val Arg Gln Ala Pro Gly Lys Gly Leu Glu Trp Val
         35                  40                  45

Ala Trp Ile Asn Thr Asn Thr Gly Glu Pro Arg Tyr Ala Glu Glu Phe
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Asp Gly Ala Tyr Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 12
<211> LENGTH: 214
<212> TYPE: PRT
<213> ORGANISM: Artificial sequence
<220> FEATURE:
<223> OTHER INFORMATION: Synthetic

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Ser Arg Phe Ser Gly
50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```